(12) United States Patent
Ennis et al.

(10) Patent No.: US 11,137,467 B2
(45) Date of Patent: Oct. 5, 2021

(54) SYSTEM AND METHOD FOR IMPROVED DIFFUSION-WEIGHTED IMAGING

(71) Applicant: The Regents of the University of California, Oakland, CA (US)

(72) Inventors: Daniel Ennis, Manhattan Beach, CA (US); Eric Aliotta, Los Angeles, CA (US); Kevin Moulin, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/488,972

(22) PCT Filed: Mar. 1, 2018

(86) PCT No.: PCT/US2018/020458
§ 371 (c)(1),
(2) Date: Aug. 27, 2019

(87) PCT Pub. No.: WO2018/160839
PCT Pub. Date: Sep. 7, 2018

(65) Prior Publication Data
US 2019/0377050 A1  Dec. 12, 2019

Related U.S. Application Data

(60) Provisional application No. 62/465,517, filed on Mar. 1, 2017.

(51) Int. Cl.
*G01R 33/563* (2006.01)
*A61B 5/055* (2006.01)
(Continued)

(52) U.S. Cl.
CPC ........ *G01R 33/56341* (2013.01); *A61B 5/055* (2013.01); *G01R 33/543* (2013.01); *G01R 33/5616* (2013.01); *G01R 33/56518* (2013.01)

(58) Field of Classification Search
CPC ............ G01R 33/56341; G01R 33/543; G01R 33/5616; G01R 33/56518; A61B 5/055
See application file for complete search history.

(56) References Cited

U.S. PATENT DOCUMENTS 4,731,583 A 3/1988 Glover
6,815,952 B1 11/2004 Rose
(Continued)

OTHER PUBLICATIONS

Aliotta E, et al. "Convex optimized diffusion encoding (CODE) gradient waveforms for minimum echo time and bulk motion-compensated diffusion-weighted MRI." Magnetic resonance in medicine 77.2 (2017): 717-729.
(Continued)

*Primary Examiner* — Gregory H Curran
(74) *Attorney, Agent, or Firm* — Quarles & Brady LLP

(57) ABSTRACT

A system and method for optimized diffusion-weighted imaging is provided. In one aspect, the method includes providing a plurality of constraints comprising an eddy current constraint for imaging a target at a selected diffusion weighting, and applying an optimization framework to generate an optimized diffusion encoding gradient waveform satisfying the plurality of constraints. The method also includes performing, using the MRI system, a pulse sequence comprising the optimized diffusion encoding gradient waveform to generate diffusion-weighted data, and generating at least one image of the target using the diffusion-weighted data.

23 Claims, 12 Drawing Sheets

(51) Int. Cl.
   *G01R 33/54* (2006.01)
   *G01R 33/561* (2006.01)
   *G01R 33/565* (2006.01)

(56) References Cited

U.S. PATENT DOCUMENTS

| | | | |
|---|---|---|---|
| 7,965,881 B2 | 6/2011 | Reese | |
| 8,587,310 B2* | 11/2013 | Taniguchi | G01R 33/56518 324/309 |
| 9,513,358 B2 | 12/2016 | Levin | |
| 2012/0271584 A1 | 10/2012 | Xu | |
| 2013/0121554 A1 | 5/2013 | Liu | |
| 2015/0146999 A1* | 5/2015 | Feiweier | G06T 5/006 382/275 |
| 2016/0187446 A1 | 6/2016 | Zhou et al. | |

OTHER PUBLICATIONS

Boesch C, et al. Temporal and spatial analysis of fields generated by eddy currents in superconducting magnets: optimization of corrections and quantitative characterization of magnet/gradient systems. Magn Reson Med. 1991;20 (2):268-84.

Finsterbusch J. Double-spin-echo diffusion weighting with a modified eddy current adjustment. Magn Reson Imaging. 2010;28(3):434-40.

Finsterbusch J. Eddy-current compensated diffusion weighting with a single refocusing RF pulse. Magn Reson Med. 2009;61(3):748-54.

Griswold MA, et al. Generalized autocalibrating partially parallel acquisitions (GRAPPA). Magn Reson Med. 2002;47(6):1202-10.

Hargreaves BA, et al. "Time-optimal multidimensional gradient waveform design for rapid imaging." MRM. 2004;51 (1):81-92.

Haselgrove JC, et al. Correction for distortion of echo-planar images used to calculate the apparent diffusion coefficient. Magn Reson Med. 1996;36(6):960-4.

International Searching Authority, International Search Report and Written Opinion for application PCT/US2018/020458, dated May 11, 2018.

Jensen DJ, et al. Reduction of pulsed gradient settling time in the superconducting magnet of a magnetic resonance instrument. Med Phys. 1987;14(5):859-62.

Jones DK, et al. Twenty-five pitfalls in the analysis of diffusion MRI data. NMRBiomed. 2010;23(7):803-20.

Koch M, et al. An assessment of eddy current sensitivity and correction in singleshot diffusion-weighted imaging. Phys Med Biol. 2000;45(12):3821-32.

Lofberg J. Automatic robust convex programming. Optimization Methods & Software. 2012;27(1):115-29.

Mansfield P, et al. Active Magnetic Screening of Coils for Static and Time-Dependent Magnetic-Field Generation in Nmr Imaging. Journal of Physics E-Scientific Instruments. 1986;19(7):540-5.

Mansfield P, et al. Active Magnetic Screening of Gradient Coils in Nmr Imaging. J Magn Reson. 1986;66(3):573-6.

Mansfield P, et al. Multishield Active Magnetic Screening of Coil Structures in Nmr. J Magn Reson. 1987;72 (2):211-23.

Meier C, et al. Concomitant field terms for asymmetric gradient coils: consequences for diffusion, flow, and echo-planar imaging. Magn Reson Med. 2008;60(1):128-34.

Middione MJ, et al. "Convex gradient optimization for increased spatiotemporal resolution and improved accuracy in phase contrast MRI." MRM. 2014;72(6):1552-64.

Pajevic S, et al. Color schemes to represent the orientation of anisotropic tissues from diffusion tensor data: application to white matter fiber tract mapping in the human brain. Magn Reson Med. 1999;42(3):526-40.

Reese TG, et al. Reduction of eddy-current-induced distortion in diffusion MRI using a twice-refocused spin echo. Magn Reson Med. 2003;49(1):177-82.

Rohde GK, et al. Comprehensive approach for correction of motion and distortion in diffusion-weighted MRI. Magn Reson Med. 2004;51(1):103-14.

Storey P, et al. Partial k-space reconstruction in single-shot diffusion-weighted echo-planar imaging. Magn Reson Med. 2007;57(3):614-9.

Trakic A, et al. Longitudinal gradient coil optimization in the presence of transient eddy currents. Magn Reson Med. 2007;57(6):1119-30.

Truong TK, et al. Correction for Eddy Current-Induced Echo-ShiftingEffect in Partial-Fourier Diffusion Tensor Imaging. Biomed Res Int. 2015;2015:185026.

Nunes, Rita G.. et al., "Performance of single spin=echo and doubly refocused diffusion-weighted sequences in the presence of eddy current fields with multiple components," Magnetic Resonance Imaging, vol. 29, No. 5, Feb. 26, 2011, pp. 659-667.

European Patent Office, Extended European Search Report and Europen Search Opinion for application 18761729.5, dated Nov. 9, 2020.

* cited by examiner

SYSTEM AND METHOD FOR IMPROVED DIFFUSION-WEIGHTED IMAGING

CROSS-REFERENCE TO RELATED APPLICATIONS

This application represents the national stage entry of International Application PCT/US2018/020458, filed on Mar. 1, 2018, which claims benefit of and priority to U.S. Provisional Application 62/465,517, filed Mar. 1, 2017, and entitled "SYSTEM AND METHOD FOR OPTIMIZED DIFFUSION-WEIGHTED IMAGING", which is incorporated herein by reference in its entirety for all purposes.

STATEMENT REGARDING FEDERALLY-SPONSORED RESEARCH/DEVELOPMENT

This invention was made with government support under R01HL131975 awarded by the National Institutes of Health. The government has certain rights in the invention.

BACKGROUND

The present disclosure relates generally to systems and methods for magnetic resonance imaging ("MRI") and, in particular, to eddy current controlled diffusion-weighted imaging ("DWI").

Any nucleus that possesses a magnetic moment attempts to align itself with the direction of the magnetic field in which it is located. In doing so, however, the nucleus precesses around this direction at a characteristic angular frequency (Larmor frequency), which is dependent on the strength of the magnetic field and on the properties of the specific nuclear species (the gyromagnetic ratio y of the nucleus). Nuclei which exhibit these phenomena are referred to herein as "spins."

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. A net magnetic moment $M_z$ is produced in the direction of the polarizing field, but the randomly oriented magnetic components in the perpendicular, or transverse, plane (x-y plane) cancel one another. If, however, the substance, or tissue, is subjected to a transient radiofrequency electromagnetic pulse (excitation field $B_1$) which is in the x-y plane and which is near the Larmor frequency, the net aligned moment, $M_z$, may be rotated, or "tipped", into the x-y plane to produce a net transverse magnetic moment Mt, which is rotating, or spinning, in the x-y plane at the Larmor frequency. The practical value of this phenomenon resides on signals that are emitted by the excited spins after the pulsed excitation signal $B_1$ is terminated. Depending upon chemically and biologically determined variable parameters such as proton density, longitudinal relaxation time ("T1") describing the recovery of $M_z$ along the polarizing field, and transverse relaxation time ("T2") describing the decay of $M_t$ in the x-y plane, this nuclear magnetic resonance ("NMR") phenomena is exploited to obtain image contrast and concentrations of chemical entities or metabolites using different measurement sequences and by changing imaging parameters.

When utilizing NMR to produce images and chemical spectra, a technique is employed to obtain NMR signals from specific locations in the subject. Typically, the region to be imaged (region of interest) is scanned using a sequence of NMR measurement cycles that vary according to the particular localization method being used. To perform such a scan, it is, of course, necessary to elicit NMR signals from specific locations in the subject. This is accomplished by employing magnetic fields ($G_x$, $G_y$, and $G_z$) which have the same direction as the polarizing field $B_0$, but which have a gradient along the respective x, y and z axes. By controlling the strength of these gradients during each NMR cycle, the spatial distribution of spin excitation can be controlled and the location of the resulting NMR signals can be identified from the Larmor frequencies typical of the local field. The acquisition of the NMR signals is referred to as sampling k-space, and a scan is completed when sufficient NMR cycles are performed to fully or partially sample k-space. The resulting set of received NMR signals are digitized and processed to reconstruct the image using various reconstruction techniques.

Diffusion-weighted imaging ("DWI") is an important MRI technique that is based on the measurement of random motion of water molecules in tissues and provides directionally dependent microstructural information across a wide range of spatial scales. DWI has been utilized for studying the anatomy of the brain, including neural architecture and brain connectivity, as well as various brain disorders, including Alzheimer's disease, schizophrenia, mild traumatic brain injury, and so forth. In particular, DWI has been widely used to estimate the apparent diffusion coefficient ("ADC") in the brain, and is considered the clinical gold standard for detection of acute and chronic stroke.

DWI commonly uses large amplitude gradient pulses to impart sensitivity to diffusion in the MRI signal amplitude. However, large gradients induce eddy currents within conductive hardware components in the MRI system, which generate additional magnetic fields affecting measured signals. To reduce the magnitude and impact of eddy currents, many systems use active gradient coil shielding, advanced gradient coil designs and gradient pre-emphasis corrections. However, substantial image distortions due to the large gradient pulses may still remain. These image distortions are especially apparent in echo planar imaging ("EPI")—the readout most commonly used in both DWI and diffusion tensor imaging ("DTI")—which is particularly sensitive to magnetic field perturbations. In addition, image distortions due to induced eddy currents are dependent on the direction and magnitude (i.e. b-value) of the diffusion encoding gradients. This leads to mis-registration between different diffusion-weighted images and confounds diffusion tensor reconstruction if not taken into account in post-processing.

Alternatives to the gradient hardware and post-processing approaches described above focus on modified pulse sequences to address images distortions. For instance, the twice refocused spin echo ("TRSE") pulse sequence has been used to reduce image distortions due to eddy currents. In particular, TRSE balances the eddy currents produced by each diffusion encoding gradient ramp by implementing a bipolar gradient encoding design and an additional refocusing pulse. Although effective in mitigating eddy current-induced distortions, TRSE significantly increases echo times ("TEs") compared to conventional diffusion encoding pulse sequences, such as monopolar ("MONO") diffusion-weighted pulse sequences. This is particularly true for low to moderate diffusion-weighting (i.e. b-values less than 1000 s/mm$^2$) and long echo-planar imaging ("EPI") readouts (i.e. greater than 50 ms) or high spatial resolution. In addition, the use of two refocusing pulses in TRSE also enhances sensitivity to $B_1$ imperfections and increases specific absorption rate ("SAR") deposition.

In light of the above, there is a need for improved imaging systems and methods sensitive to diffusion that also address eddy currents induced by magnetic field gradients.

SUMMARY

The present disclosure overcomes the drawbacks of previous technologies by providing a system and method directed to diffusion-weighted imaging ("DWI"). Specifically, an optimization framework is used herein to generate diffusion encoding gradient waveforms for acquiring diffusion-weighted images. In this framework, various constraints are simultaneously satisfied and desired objectives are optimized, including minimizing temporal footprint. In particular, eddy current compensation is incorporated in the optimization framework, in addition to satisfying imaging and hardware constraints. In this manner, diffusion-weighted images, such as diffusion tensor images ("DTI"), may be free of eddy current distortions. In some aspects, diffusion-weighted images can be produced using a single refocusing pulse, thereby reducing sensitivity to $B_1$ imperfections and SAR deposition.

In accordance with one aspect of the disclosure, a method for generating images using a magnetic resonance imaging ("MRI") is provided. The method includes providing a plurality of constraints comprising an eddy current constraint for imaging a target at a selected diffusion weighting, and applying an optimization framework to generate an optimized diffusion encoding gradient waveform satisfying the plurality of constraints. The method also includes performing, using the MRI system, a pulse sequence comprising the optimized diffusion encoding gradient waveform to generate diffusion-weighted data, and generating at least one image of the target using the diffusion-weighted data.

In accordance with another aspect of the disclosure, a magnetic resonance imaging ("MRI") system is provided. The system includes a magnet system configured to generate a polarizing magnetic field about at least a region of interest ("ROI") of a subject arranged in the MRI system, a plurality of gradient coils configured to apply a gradient field with respect to the polarizing magnetic field, and a radio frequency ("RF") system configured to apply RF excitation fields to the subject and acquire MR image data therefrom. The system also includes a computer programmed to receive an indication of a plurality of constraints comprising an eddy current constraint for imaging the ROI at a selected diffusion weighting, and apply an optimization framework to generate an optimized diffusion encoding gradient waveform satisfying the plurality of constraints. The computer is also programmed to direct the plurality of gradient coils and RF system to perform a pulse sequence comprising the optimized diffusion encoding gradient waveform to generate diffusion-weighted data, and generate at least one image of the target using the diffusion-weighted data.

The foregoing and other advantages of the invention will appear from the following description.

BRIEF DESCRIPTION OF THE DRAWINGS

The present invention will hereafter be described with reference to the accompanying drawings, wherein like reference numerals denote like elements.

DETAILED DESCRIPTION

Diffusion-weighted imaging, among other magnetic resonance imaging ("MRI") techniques, can provide invaluable information about the structure and function of various tissues in the body. In a diffusion-weighted pulse sequence, a pair of diffusion encoding gradients, or gradient waveforms, are typically applied along a given direction to attenuate the transversal magnetization in a volume of tissue. The detected signal intensity depends on the diffusion of water within the tissue being imaged. The "b-value" of a diffusion-weighted pulse sequence (measured in units of s/mm$^2$) indicates the degree of diffusion-weighting in an acquired image and dictates the level of signal attenuation as a function of tissue diffusivity. The b-value is determined in general by the strength and duration of the applied gradients and in some cases by the time interval between applied gradients. Higher b-values increase the effect of diffusion on the signal and decrease the overall signal intensity.

Figure 1:
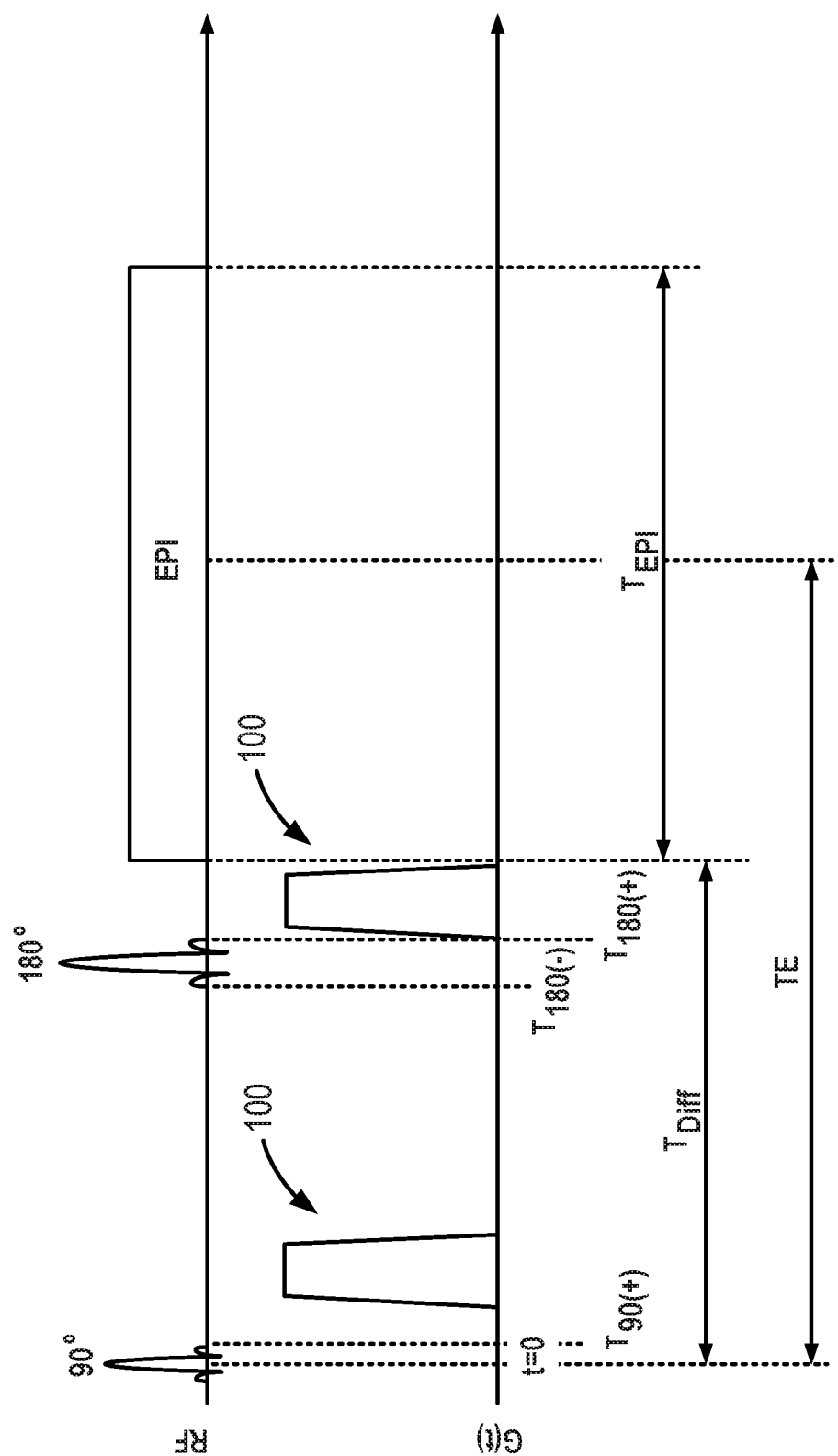
FIG. 1 is a schematic diagram illustrating an example monopolar ("MONO") diffusion-weighted pulse sequence.

Traditionally, diffusion-weighted imaging ("DWI") uses a Spin-Echo Echo Planar Imaging ("SE-EPI") pulse sequence with large, motion sensitizing diffusion encoding gradients. FIG. 1 shows an example monopolar ("MONO") gradient encoding SE-EPI pulse sequence that is widely available and relatively fast. Although MONO produces moderate signal-to-noise ratios ("SNR") and spatial resolution, the sequence is very sensitive to bulk motion, and includes a dead time that extends the overall diffusion encoding temporal footprint. In addition, the large, motion-sensitizing gradients 100 introduce eddy currents that cause image distortions.

Eddy currents are produced within various conductive MRI hardware components during applied time-varying gradient pulses, and specifically during ramp-up and ramp-down intervals, and exponentially decay over time. When equivalent ramp-up and ramp-down intervals are used, such as the case of the trapezoidal gradient waveforms in MONO pulse sequence of FIG. 1, eddy currents are equal in magnitude and opposite in direction. However, the amount decay of the eddy currents between the ramp-up and ramp-down intervals is different because of their occurrence at different time points in the pulse sequence. This leads to imperfect cancellation and a non-zero superposition of the eddy current induced magnetic fields. Such magnetic fields can persist during the echo-planar imaging ("EPI") readout and can result in deviations from the target k-space trajectory and substantial image distortions.

In addition to addressing eddy current induced image distortions, it is recognized herein that a number of imaging and hardware constraints are also to be considered in designing a diffusion-weighted pulse sequence. For instance, diffusion encoding gradients need to be off during application of RF pulses and readout. In addition, diffusion encoding gradient waveforms need also conform to target b-values, gradient moment values, as well as hardware capabilities of the imaging system, such as maximum gradient amplitude and slew rate. However, obtaining closed-form gradient waveforms in a diffusion-weighted pulse sequence that can satisfy most or all imaging and hardware constraints and are time-optimal can be tremendously difficult, if not impossible. Hence, prior approaches have typically utilized general guidelines to develop pulse sequences (such as using trapezoidal diffusion gradients, and symmetrical arrangements), that often come at the expense of imaging speed or quality, as described.

Therefore, in accordance with the present disclosure, a system and method implementing an optimization framework that incorporates eddy current compensation or nulling, in addition to imaging and hardware considerations, to produce enhanced diffusion-weighted images is described herein. In this framework, optimized diffusion encoding gradient waveforms that satisfy a number constraints, including eddy current constraints, are generated without need for restricting gradient waveform shape. In addition, a number of objectives, such as minimized echo time, are also taken into consideration in this optimization framework. In some aspects, a convex optimization approach may be utilized, as will be described. To this end, the optimization framework is a convex optimized diffusion encoding ("CODE") framework. In addition, when eddy constraints are taken into consideration, resultant gradient waveforms are eddy current nulled convex optimized diffusion encoding ("EN-CODE") gradient waveforms. However, it may be readily appreciated by one of ordinary skill in the art that the optimization framework described could include a non-convex optimization, as well as other optimization approaches.

As appreciated from description herein, in addition to addressing eddy current, motion and other imaging issues, the present approach can significantly shorten the echo time ("TE") in a Spin-Echo Echo Planar Imaging ("SE-EPI") pulse sequence, for example, and improve signal-to-noise ratios ("SNR"). In some aspects, the time between the RF excitation and refocusing pulses in a SE-EPI pulse sequence can be effectively utilized to decrease TE. Also, optimized diffusion encoding gradient waveforms generated using the herein provided system and method may be asymmetric about the refocusing pulse. Although discussion provided herein refers to a SE-EPI pulse sequence, one of ordinary skill in the art would recognize that present approach is applicable more broadly to other diffusion-weighted pulse sequences. As non-limiting examples, the present framework could be implemented using a stimulated echo acquisition mode ("STEAM") pulse sequence, a turbo spin echo ("TSE") pulse sequence, and others.

As described, the present optimization framework can be used to generate optimized diffusion encoding gradients that satisfy a number of constraints, including eddy current constraints, gradient constraints, gradient moment constraints, and hardware constraints. In particular, gradient constraints include diffusion encoding gradient magnitude and timing constraints, such as gradients being off during RF activity and during the data acquisition. With particular reference to the example SE-EPI pulse sequence of FIG. 1, diffusion encoding gradients are zero during both RF excitation pulses and RF refocusing pulses, as well as during the EPI readout. In mathematical form, this may be expressed:

$$G(0 \leq t \leq T_{90(+)}) = 0 \qquad \text{Eqn. (1A)}$$

$$G(T_{180(-)} \leq t \leq T_{180(+)}) = 0 \qquad (1B)$$

$$G(T_{Diff} \leq t \leq TE) = 0 \qquad (1C)$$

where diffusion encoding begins at $t=T_{90(+)}$ (referring to the time immediately after 90° RF excitation pulse and EPI correction lines), the 180° RF refocusing pulse is played out when $T_{180(-)} \leq t \leq T_{180(+)}$, and the EPI readout occurs when $T_{Diff} \leq t \leq T_{Diff} + T_{EPI}$ (where $T_{EPI}$ is the EPI readout duration). The period of time between the initial excitation (t=0) and the portion of the EPI readout where the center k-space line is read is given by the echo time, TE. For full-Fourier imaging, $TE = T_{Diff} + 0.5 * T_{EPI}$, for example.

Also, optimized diffusion encoding gradient waveforms may satisfy gradient moment constraints, as described. This may include having M0 nulled at the end of diffusion encoding (i.e. $t=T_{Diff}$ in FIG. 1), and, as required, having nulled M1, or M1 and M2. These gradient moment constraints may be expressed as:

$$M_0 = \int_0^{T_{Diff}} G(t) dt = 0 \qquad \text{Eqn. (2A)}$$

$$M_0 = \int_0^{T_{Diff}} t G(t) dt = 0 \qquad (2B)$$

$$M_2 = \int_0^{T_{Diff}} t^2 G(t) dt = 0 \qquad (2C)$$

The imaging gradients played during the EPI readout have zero net M0, and negligible M1, and M2 at the TE (<1% of typical moments from MONO). Therefore if they are nulled end of diffusion encoding (i.e. $t=T_{Diff}$ in FIG. 1), they would also effectively nulled at t=TE. The moments of the slice select gradient, which may also be negligible (less than 0.5% of typical diffusion encoding gradient moments for MONO) with respect to the diffusion encoding gradients, were not, but could be, considered in this optimization. Although Eqns. 2 indicate gradient moment constraints for M0, M1 and M2, it is envisioned that the present approach may be readily extended to any combination of gradient moment constraints, including higher order gradient moments, such as M3, M4, and so forth.

From a practical standpoint, designed gradient waveforms must also adhere to gradient hardware limitations, or hardware constraints, including maximum gradient amplitude ("$G_{max}$") and slewrate ("$SR_{max}$"). These constraints may be expressed as:

$$G(t) \leq G_{max} \quad \text{Eqn. (3A)}$$

$$\dot{G}(t) \leq SR_{max} \quad \text{(3B)}$$

In addition, as described, the present optimization framework takes into account eddy currents induced by applied gradients. In particular, eddy currents from an arbitrary gradient waveform G(t) can be modeled using an RL-circuit model. An induced magnetic field $B_{EC}$ can then be expressed as:

$$B_{EC}(t) = \sum_i w(\lambda_i)\left(\frac{dG}{dt} * e^{-\frac{t}{\lambda_i}}\right) \quad \text{Eqn. (4)}$$

where * is the convolution operator, $\lambda_i$ are the time constants of eddy current decay, and w are system-dependent scaling factors for respective $\lambda_i$. In the case that a single $\lambda$ is considered, then Eqn. 4 reduces to:

$$B_{EC}(\lambda, t) = w(\lambda)\frac{dG}{dt} * e^{-\frac{t}{\lambda}} \quad \text{Eqn. (5)}$$

It is recognized that the scanner-dependent, scalar values of w need not be known in order to null eddy currents for any single $\lambda$ if the convolution term can be minimized at a specific time. Therefore, a new function $\varepsilon$, that is proportional to $B_{EC}$ and independent of w, may be defined as follows:

$$\varepsilon(\lambda, t) = \frac{dG}{dt} * e^{-\frac{t}{\lambda}} \quad \text{Eqn. (6)}$$

An eddy current constraint can then be defined using Eqn. 6, as follows:

$$\varepsilon(\lambda_{null}, T_{Diff}) = 0 \quad \text{Eqn. (7)}$$

where $T_{Diff}$ is the time corresponding to the end of diffusion encoding and $\lambda_{null}$ is the target decay constant to be nulled. Importantly, nulling eddy currents at $T_{Diff}$ ensures that eddy current contributions from the diffusion encoding gradient waveform are zero after $T_{Diff}$, namely $t \geq T_{Diff}$. As described, the eddy current constraint ensures that the effects of induced eddy currents from the diffusion encoding gradient waveform are nullified to eliminate image distortions. In some aspects, eddy current-induced magnetic field values are negligible during readout. That is, induced magnetic fields are either zero during readout, due to eddy currents having fully decayed, or substantially consistent during readout, with eddy currents being constant across all desired diffusion encoding directions. Such, non-zero or constant magnetic fields would not contribute to misregistration and other undesired effects.

Comparing the magnitude of eddy current induced artifacts between two different pulse sequences is typically an empirical exercise. Note, however, that Eqn. 6 can also be used to define the eddy current characteristics of any diffusion encoding gradient waveform, referred to herein as eddy current spectrum. By calculating $\varepsilon(\lambda, t)$ over a range of $\lambda$, and at the end of diffusion encoding ($T_{Diff}$), the eddy current spectrum can be compared between different diffusion encoding gradient waveforms. It is noted that because w is not included in this formulation, the eddy current spectrum is system invariant.

As described, the magnitude of diffusion-weighting in a DWI acquisition is characterized by the b-value, which is given by:

$$b = \gamma^2 \int_0^{T_{Diff}} F(t)^2 dt \quad \text{Eqn. (8)}$$

where $$F(t) = \int_0^t G(\tau) d\tau \quad \text{Eqn. (9)}$$

In Eqn. 8, G(t) is the gradient amplitude as a function of time, $T_{Diff}$ is the time at the end of the diffusion encoding gradient waveform, and $\gamma$ is the gyromagnetic ratio of 1H. The time t=0 may correspond with the center of an RF excitation pulse. The optimization to obtain optimized diffusion encoding gradient waveforms, satisfying various constraints as described above, may then be carried out by determining a maximum b-value for a fixed TE or selected sequence timing, and iteratively reducing the TE until the maximum b-value is equivalent to a target b-value.

Figure 2:
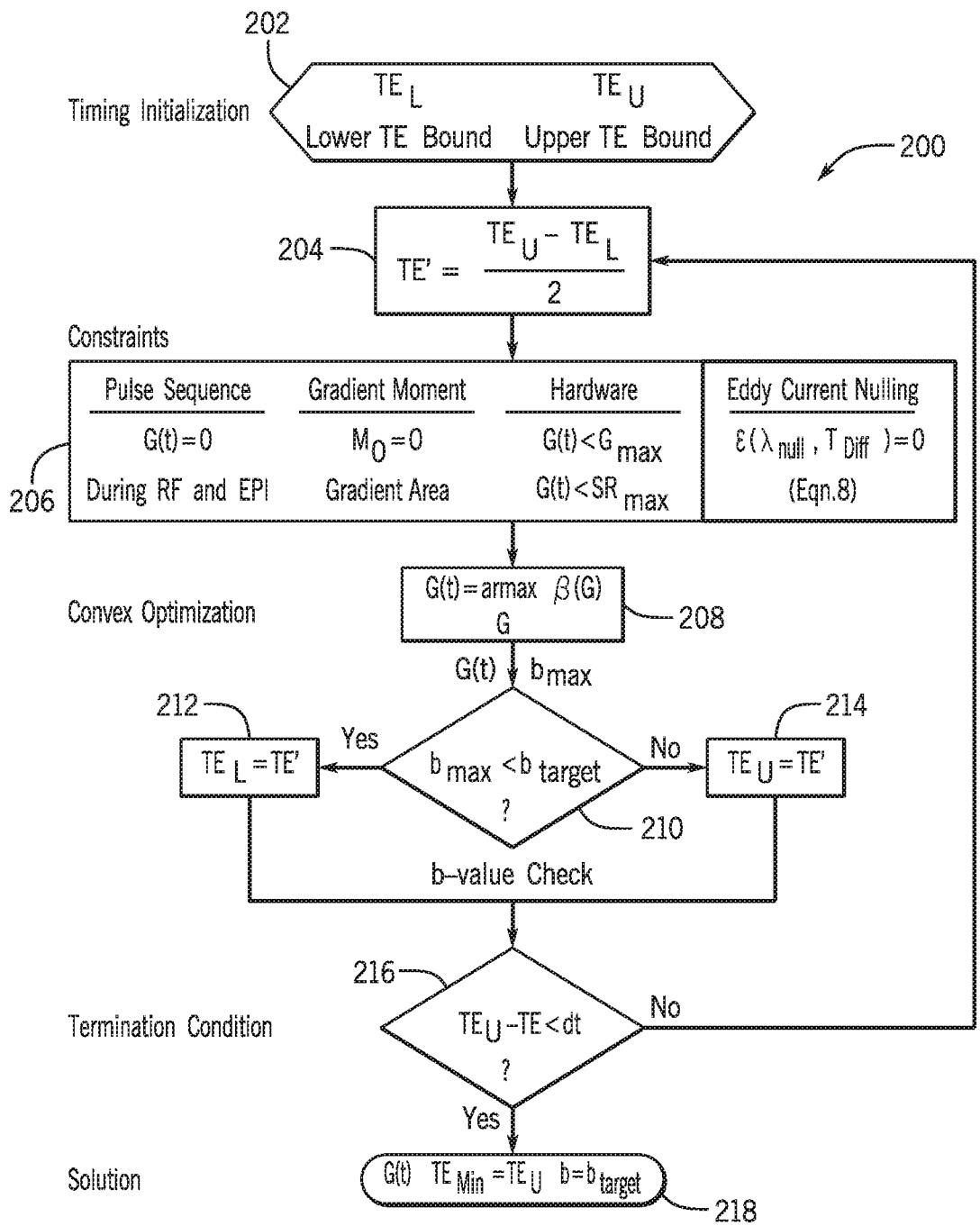
FIG. 2 is a flowchart setting forth steps of a process, in accordance with aspects of the present disclosure.

This is illustrated in FIG. 2, which shows a flowchart illustrating steps of a process 200 for generating optimized diffusion encoding gradient waveforms, in accordance with aspects of present disclosure. Although process 200 shows specific steps and implementations, indeed various modifications would be apparent to one of ordinary skill in the art, and such modifications may still be considered within the scope of the present approach.

The process 200 may begin with a timing initialization, as indicated by process block 202, which establishes initial values for lower and upper TE bounds, $TE_L$ and $TE_U$, respectively. Such values may be selected in accordance with desired diffusion-weighted images and pulse sequence utilized. A target b-value, $b_{target}$, may also be provided at this step. In some aspects, $TE_U$ may be defined in accordance with the TE of a non-optimized sequence with the desired gradient moments (i.e., monopolar for M0=0, bipolar for M0=M1=0, modified bipolar for M0=M1=M2=0) and some additional time value to accommodate the time needed for eddy current nulling. For example, for an M0 nulled, eddy current nulled waveform, $TE_U$ may be defined by the monopolar TE plus about 20 ms. Also, $TE_L$ may be defined by the TE of an equivalent spin echo sequence (i.e., without diffusion encoding gradients), which has a minimum TE of $2 \cdot (0.5 \cdot T_{180} + T\varepsilon)$ (FIG. 1).

Following computation $TE' = (TE_L - TE_U)/2$, as indicated by process block 204, a number of constraints are provided at process block 206. As shown in FIG. 2, the constraints may include gradient constraints (Eqns. 1), gradient moment constraints (Eqns. 2), hardware constraints (Eqns. 3) and eddy current constraints (Eqn. 7). The combination of constraints may depend upon specific imaging requirements, such as requirements for controlling eddy currents, bulk motion, and hardware requirements.

Then, at process block 208, at least one objective functional is determined based on the provided constraints. In some aspects, the objective functional(s) may be configured to reflect other objectives, constraints, or terms, including Maxwell terms, simulation thresholds, noise/sound pressure, eddy currents, and others. Specifically, the b-value in Eqn. 8 is a convex functional of G(t) (i.e. its second variation is positive definite) and therefore does not necessarily have a single maximum. In addition, Eqn. 8 is not a unique functional of G(t), which means that multiple waveforms can produce the same b-value (e.g., +G(t) and −G(t) have the same b-value). Therefore, to facilitate optimization, the objective function can be reformulated by defining the function, β as follows:

$$\beta = \int_0^{TDiff} F(t)dt \quad \text{Eqn. (10)}$$

The magnitude of β corresponds directly with the b-value, but it is a concave functional of G(t) (i.e. its second variation is negative definite); therefore it contains a maximum that can be determined. Consequently, the gradient waveform G(t) that produces the maximum β (and thus the maximum b-value) can be determined using the following objective function:

$$G(t) = \underset{G}{\operatorname{argmax}} \beta(G) \quad \text{Eqn. (11)}$$

A convex optimization may then be carried out to generate a solution for optimized diffusion encoding gradient waveforms, where G(t) may be defined discretely on t=m·dt where dt is the temporal resolution of the optimization and m is an integer between 1 and $T_{Diff}$/dt.

The optimization begins by determining a maximum b-value, $b_{max}$, for a fixed TE', and then subsequently adjusting the TE' until the maximum is equivalent to $b_{target}$. As shown in FIG. 2, this includes evaluating the condition $b_{max} < b_{target}$ at decision block 210, and based whether true or not, setting $TE_L$=TE' or $TE_U$=TE', as indicated by process block 212 and 214 respectively. Then, at decision block 216, an evaluation is made for the termination condition $TE_U$-$TE_L \leq dt$. If not satisfied, the process 200 continues with process block 204. Otherwise, a time optimal solution is reached at process block 218, having an optimized diffusion encoding gradient waveform G(t), that satisfies the target b-value and reaches a minimized TE. As appreciated from FIG. 2, the optimization problem can be efficiently solved through successive binary searches that divide the TE search space with each iteration of Eqn. 7. The optimized diffusion encoding gradient waveform may then be included in a pulse sequence that is executed to generate diffusion-weighted images.

Figure 3:
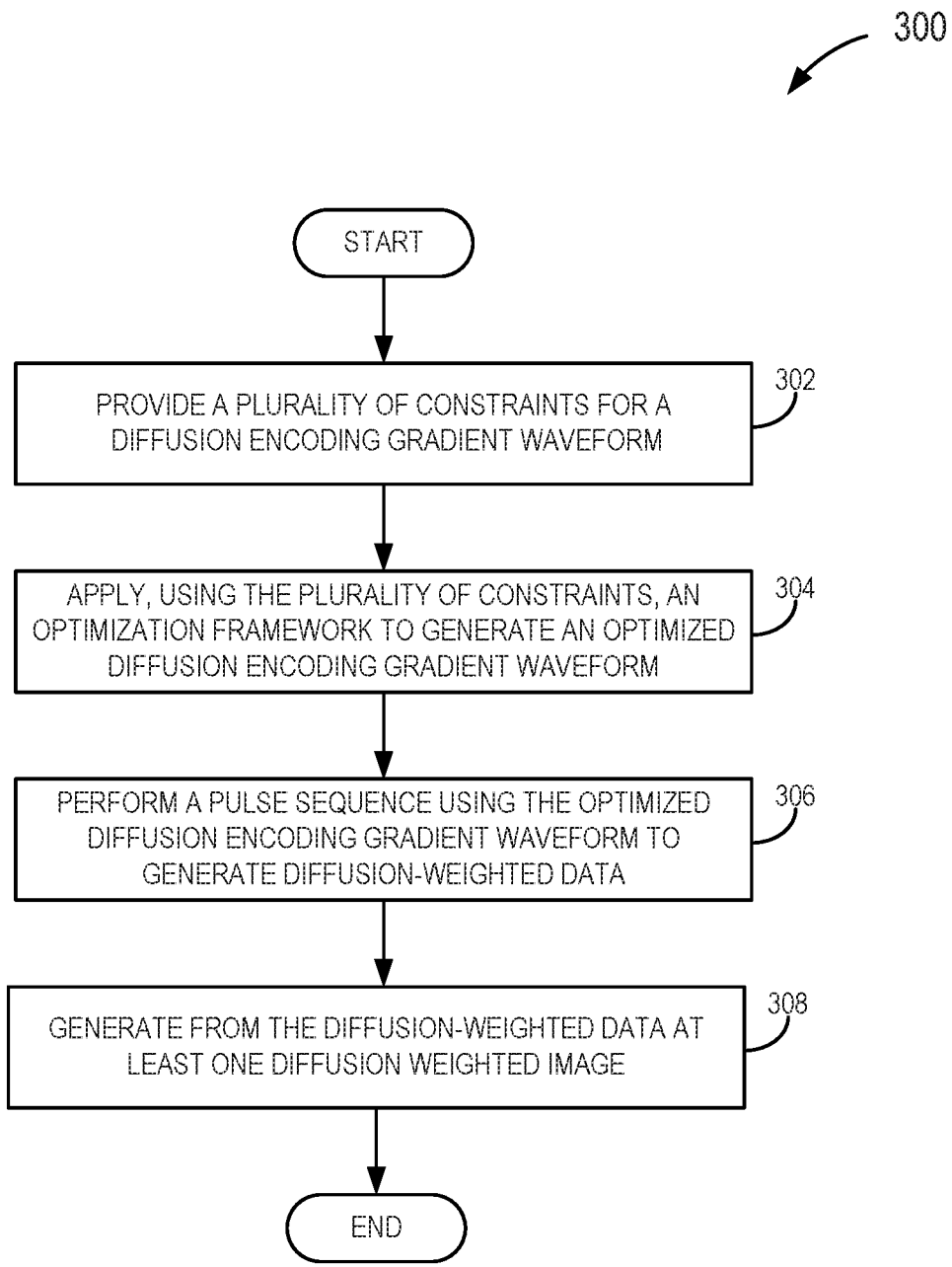
FIG. 3 is a flowchart setting forth steps of a process, in accordance with aspects of the present disclosure.

FIG. 3 is a flowchart setting forth steps of a process 300, in accordance with aspects of a method of the present disclosure. This process 300 may be carried out using a magnetic resonance imaging ("MRI") system, as will be described with reference to FIG. 4, or any suitable system. In some aspects, the process 300 may be embodied using software or instructions stored in non-transitory computer-readable media.

The process 300 may begin at process block 302 with providing a plurality of constraints for imaging a target at a selected diffusion weighting. As described, this may include providing gradient constraints, gradient moment constraints, hardware constraints, eddy current constraints, as well as other objectives. In some aspects, an indication may also be provided at process block 302 with respect to the imaging pulse sequence being utilized. For example, the indication may include parameters associated with a SE-EPI pulse sequence, including desired field-of-view, spatial resolution, SNR, and so forth. In addition, the indication may include a selected b-value, or diffusion-weighting, and applied gradient directions.

Then, at process block 304, an optimization framework, such as a convex optimization framework, may be applied to generate an optimized diffusion encoding gradient waveform. As described with reference to FIG. 2, this process includes generating an objective function based on the provided constraints, (Eqn. 11) and other objectives, and obtaining solution for the gradient waveform, based on the selected b-value, using an iterative process. As described, the iterative process may be performed to minimize pulse sequence timing parameters, such as TE, gradient duration during the diffusion encoding period(s), and other timings.

Figure 6A:
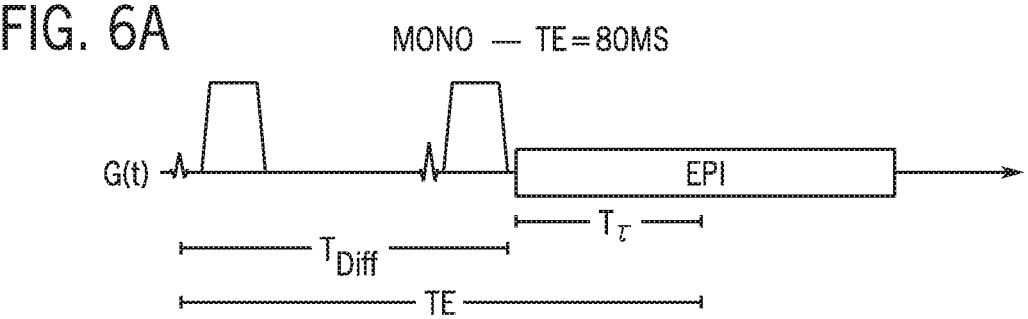
FIG. 6A is a pulse sequence diagram of a MONO pulse sequence in accordance with aspects of the present disclosure.
Figure 6B:
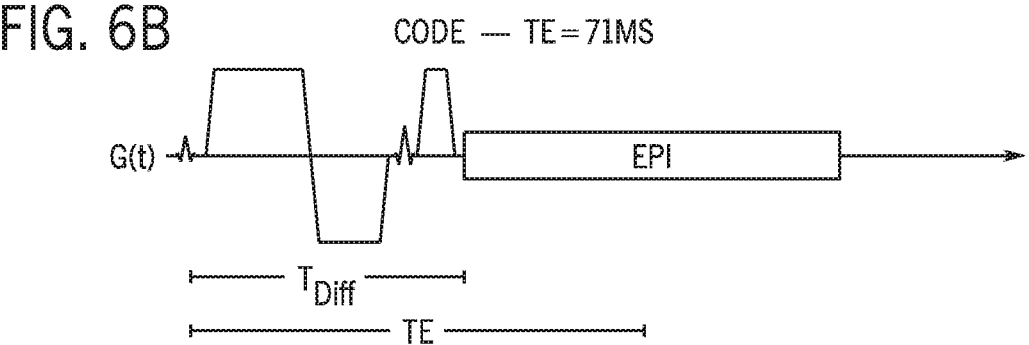
FIG. 6B is a pulse sequence diagram of a CODE pulse sequence in accordance with aspects of the present disclosure.
Figure 6C:
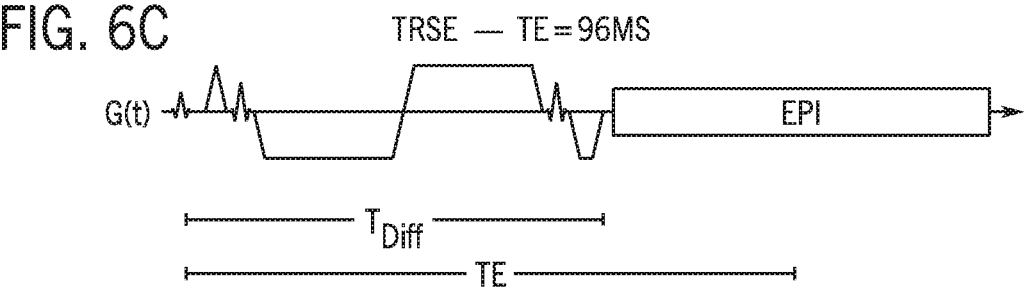
FIG. 6C is a pulse sequence diagram of a TRSE pulse sequence in accordance with aspects of the present disclosure.
Figure 6D:
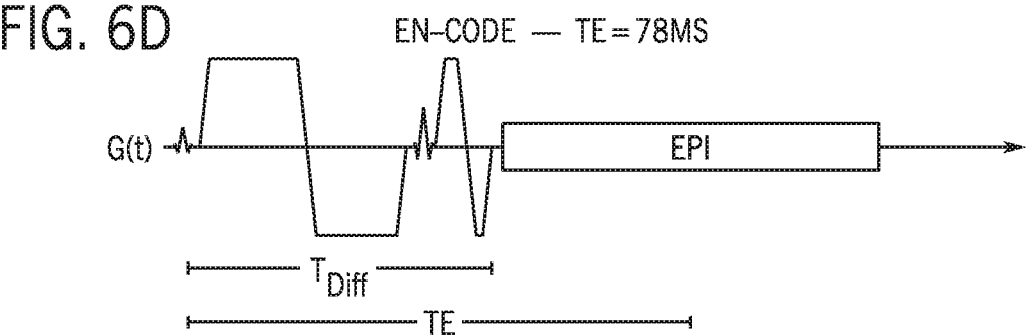
FIG. 6D is a pulse sequence diagram of a EN-CODE pulse sequence in accordance with aspects of the present disclosure.

The optimized diffusion encoding gradient waveform may then be used in a pulse sequence to generate diffusion-weighted data, as indicated by process block 306. By way of example, FIGS. 6B and 6D show non-limiting SE-EPI pulse sequences incorporating optimized diffusion encoding gradient waveforms in accordance with the present approach. As appreciated from the figures, various gradient waveforms (in dependence of the indicated constraints) may be played out between the RF excitation, refocusing pulses, and EPI data acquisition. It may be appreciated that various pulse sequences, including various data acquisitions and k-space sampling trajectories may be utilized at process block 306. The pulse sequence may be repeated for any number of times, and for any gradient directions, depending on the imaged structures, image type, and amount of diffusion-weighted data sufficient for desired SNR.

Referring again to FIG. 3, from the diffusion-weighted data obtained at process block 306, at least one image may be generated at process block 308 using various image reconstruction techniques and methods. Non-limiting examples of images generated at process block 308 include diffusion-weighted images, ADC maps, diffusion tensor images ("DTIs"), diffusion restriction images, fractional anisotropy ("FA") maps, mean diffusivity ("MD") maps, radial diffusivity ("RD") maps, axial diffusivity ("AD") maps, and higher order q-space images. In some aspects, gradient directions to be sampled are accounted for in the optimization.

Figure 4:
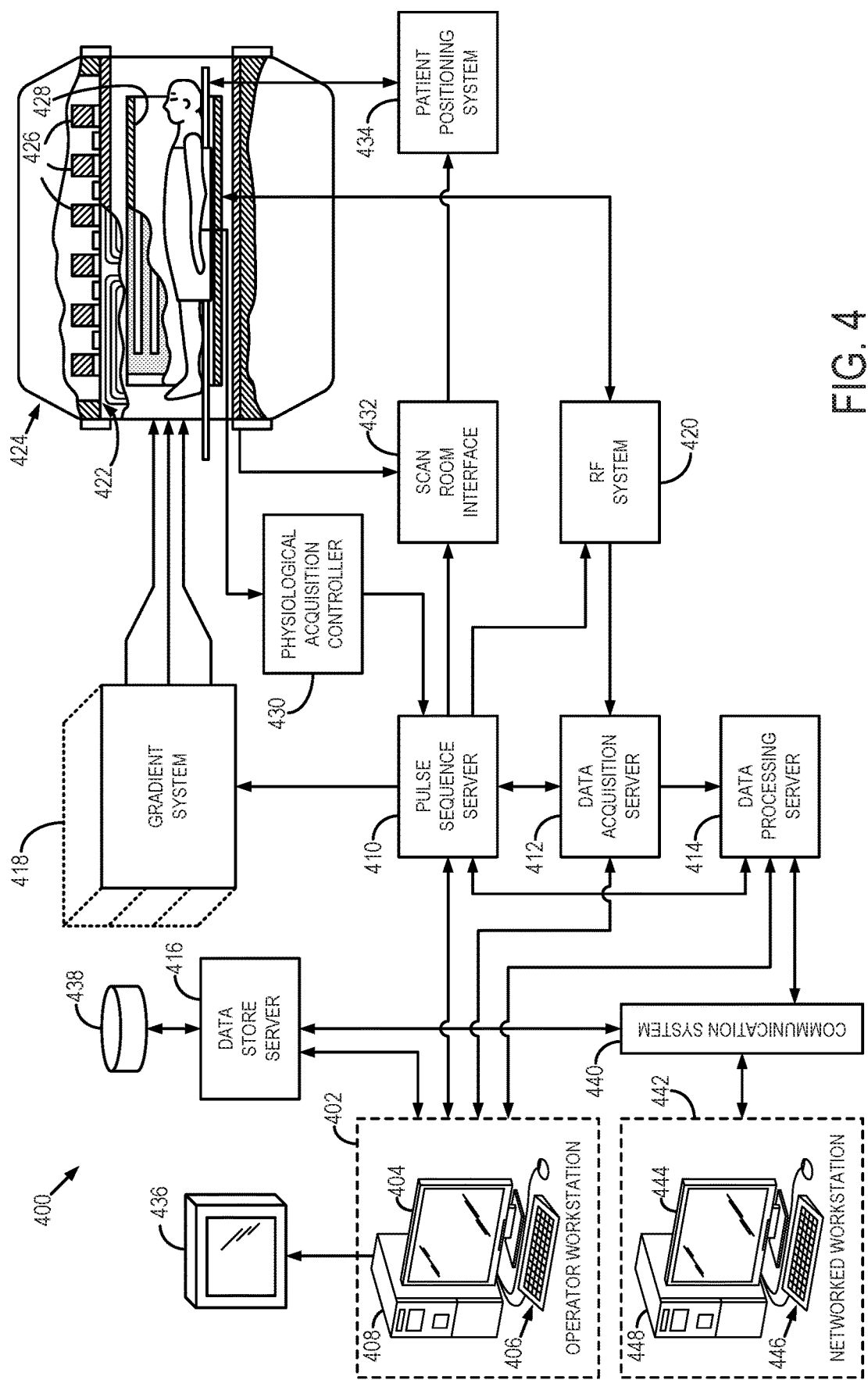
FIG. 4 is a schematic diagram of a magnetic resonance imaging system, in accordance with aspects of the present disclosure.

Referring now particularly to FIG. 4, an example of an MRI system 400, in accordance with aspects of the present disclosure, is illustrated. The MRI system 400 includes a workstation 402 having a display 404 and a keyboard 406. The workstation 402 includes a processor 408, such as a commercially available programmable machine running a commercially available operating system. The workstation 402 provides the operator interface that enables scan prescriptions to be entered into the MRI system 400. The workstation 402 is coupled to servers, including a pulse sequence server 410, a data acquisition server 412, a data processing server 414, and a data store server 416. The workstation 402 and each server 410, 412, 414, and 416 are in communication.

The pulse sequence server 410 functions in response to instructions downloaded from the workstation 402 to operate a gradient system 418 and a radiofrequency ("RF")

system 420. Gradient waveforms necessary to perform the prescribed scan are produced and applied to the gradient system 418, which excites gradient coils in an assembly 422 to produce the magnetic field gradients $G_x$, $G_y$, and $G_z$ used for position encoding MR signals. The gradient coil assembly 422 forms part of a magnet assembly 424 that includes a polarizing magnet 426 and a whole-body RF coil 428.

RF excitation waveforms are applied to the RF coil 428, or a separate local coil (not shown in FIG. 4), by the RF system 420 to perform the prescribed magnetic resonance pulse sequence. Responsive MR signals detected by the RF coil 428, or a separate local coil, are received by the RF system 420, amplified, demodulated, filtered, and digitized under direction of commands produced by the pulse sequence server 410. The RF system 420 includes an RF transmitter for producing a wide variety of RF pulses used in MR pulse sequences. The RF transmitter is responsive to the scan prescription and direction from the pulse sequence server 410 to produce RF pulses of the desired frequency, phase, and pulse amplitude waveform. The generated RF pulses may be applied to the whole body RF coil 428 or to one or more local coils or coil arrays.

The RF system 420 also includes one or more RF receiver channels. Each RF receiver channel includes an RF preamplifier that amplifies the MR signal received by the coil 428 to which it is connected, and a detector that detects and digitizes the I and Q quadrature components of the received MR signal. The magnitude of the received MR signal may thus be determined at any sampled point by the square root of the sum of the squares of the I and Q components:

$$M = \sqrt{I^2 + Q^2} \qquad \text{Eqn. (12)}$$

and the phase of the received MR signal may also be determined:

$$\varphi = \tan^{-1}\left(\frac{Q}{I}\right). \qquad \text{Eqn. (13)}$$

The pulse sequence server 410 also optionally receives patient data from a physiological acquisition controller 430. The controller 430 receives signals from a number of different sensors connected to the patient, such as electrocardiograph ("ECG") signals from electrodes, or respiratory signals from a bellows or other respiratory monitoring device. Such signals are typically used by the pulse sequence server 410 to synchronize, or "gate," the performance of the scan with the subject's heart beat or respiration.

The pulse sequence server 410 also connects to a scan room interface circuit 432 that receives signals from various sensors associated with the condition of the patient and the magnet system. It is also through the scan room interface circuit 432 that a patient positioning system 434 receives commands to move the patient to desired positions during the scan.

The digitized MR signal samples produced by the RF system 420 are received by the data acquisition server 412. The data acquisition server 412 operates in response to instructions downloaded from the workstation 402 to receive the real-time MR data and provide buffer storage, such that no data is lost by data overrun. In some scans, the data acquisition server 412 does little more than pass the acquired MR data to the data processor server 414. However, in scans that require information derived from acquired MR data to control the further performance of the scan, the data acquisition server 412 is programmed to produce such information and convey it to the pulse sequence server 410. For example, during prescans, MR data is acquired and used to calibrate the pulse sequence performed by the pulse sequence server 410. Also, navigator signals may be acquired during a scan and used to adjust the operating parameters of the RF system 420 or the gradient system 418, or to control the view order in which k-space is sampled. In all these examples, the data acquisition server 412 acquires MR data and processes it in real-time to produce information that is used to control the scan.

The data processing server 414 receives MR data from the data acquisition server 412 and processes it in accordance with instructions downloaded from the workstation 402. Such processing may include, for example: Fourier transformation of raw k-space MR data to produce two or three-dimensional images; the application of filters to a reconstructed image; the performance of a backprojection image reconstruction of acquired MR data; the generation of functional MR images; and the calculation of motion, flow, or diffusion-weighted images.

Images reconstructed by the data processing server 414 are conveyed back to the workstation 402 where they are stored. Real-time images are stored in a data base memory cache, from which they may be output to operator display 412 or a display 436 that is located near the magnet assembly 424 for use by attending physicians. Batch mode images or selected real time images are stored in a host database on disc storage 438. When such images have been reconstructed and transferred to storage, the data processing server 414 notifies the data store server 416 on the workstation 402.

The MRI system 400 may also include one or more networked workstations 442. By way of example, a networked workstation 442 may include a display 444, one or more input devices 446 (such as a keyboard and mouse or the like), and a processor 448. The networked workstation 442 may be located within the same facility as the operator workstation 402, or in a different facility, such as a different healthcare institution or clinic. The networked workstation 442 may include a mobile device, including phones or tablets.

The networked workstation 442, whether within the same facility or in a different facility as the operator workstation 402, may gain remote access to the data processing server 414 or data store server 416 via the communication system 440. Accordingly, multiple networked workstations 442 may have access to the data processing server 414 and the data store server 416. In this manner, magnetic resonance data, reconstructed images, or other data may be exchanged between the data processing server 414 or the data store server 416 and the networked workstations 442, such that the data or images may be remotely processed by a networked workstation 442. This data may be exchanged in any suitable format, such as in accordance with the transmission control protocol ("TCP"), the internet protocol ("IP"), or other known or suitable protocols.

Embodiments of the present technology may be described herein with reference to flowchart illustrations of methods and systems according to embodiments of the technology, and/or procedures, algorithms, steps, operations, formulae, or other computational depictions, which may also be implemented as computer program products. In this regard, each block or step of a flowchart, and combinations of blocks (and/or steps) in a flowchart, as well as any procedure, algorithm, step, operation, formula, or computational depiction can be implemented by various means, such as hardware, firmware, and/or software including one or more computer program instructions embodied in computer-readable program code. As will be appreciated, any such computer program instructions may be executed by one or more computer processors, including without limitation a general purpose computer or special purpose computer, or other programmable processing apparatus to produce a machine, such that the computer program instructions which execute on the computer processor(s) or other programmable processing apparatus create means for implementing the function(s) specified.

Accordingly, blocks of the flowcharts, and procedures, algorithms, steps, operations, formulae, or computational depictions described herein support combinations of means for performing the specified function(s), combinations of steps for performing the specified function(s), and computer program instructions, such as embodied in computer-readable program code logic means, for performing the specified function(s). It will also be understood that each block of the flowchart illustrations, as well as any procedures, algorithms, steps, operations, formulae, or computational depictions and combinations thereof described herein, can be implemented by special purpose hardware-based computer systems which perform the specified function(s) or step(s), or combinations of special purpose hardware and computer-readable program code.

Furthermore, these computer program instructions, such as embodied in computer-readable program code, may also be stored in one or more computer-readable memory or memory devices that can direct a computer processor or other programmable processing apparatus to function in a particular manner, such that the instructions stored in the computer-readable memory or memory devices produce an article of manufacture including instruction means which implement the function specified in the block(s) of the flowchart(s). The computer program instructions may also be executed by a computer processor or other programmable processing apparatus to cause a series of operational steps to be performed on the computer processor or other programmable processing apparatus to produce a computer-implemented process such that the instructions which execute on the computer processor or other programmable processing apparatus provide steps for implementing the functions specified in the block(s) of the flowchart(s), procedure (s) algorithm(s), step(s), operation(s), formula(e), or computational depiction(s).

It will further be appreciated that the terms "programming" or "program executable" as used herein refer to one or more instructions that can be executed by one or more computer processors to perform one or more functions as described herein. The instructions can be embodied in software, in firmware, or in a combination of software and firmware. The instructions can be stored local to the device in non-transitory media, or can be stored remotely such as on a server, or all or a portion of the instructions can be stored locally and remotely. Instructions stored remotely can be downloaded (pushed) to the device by user initiation, or automatically based on one or more factors.

It will further be appreciated that as used herein, that the terms processor, computer processor, central processing unit ("CPU"), and computer are used synonymously to denote a device capable of executing the instructions and communicating with input/output interfaces and/or peripheral devices, and that the terms processor, computer processor, CPU, and computer are intended to encompass single or multiple devices, single core and multicore devices, and variations thereof.

The above-described system and method may be further understood by way of examples. These examples are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

EXAMPLE

The following is a non-limiting example illustrating concepts of the present disclosure. In particular, eddy current nulled convex optimized diffusion encoding ("EN-CODE") gradient waveforms, obtained using an optimization framework in accordance with the present disclosure, can result produce imaging efficiently and free of eddy current induced image distortions. Specifically, eddy current compensated diffusion encoding waveforms were used to generate diffusion tensor imaging ("DTI"). The DTI were then compared to images obtained using the existing pulse sequence methods attempting to address eddy currents, including a twice refocused spin echo ("TRSE") pulse sequence and monopolar ("MONO") pulse sequence, as well as images obtained using non-eddy current compensated CODE.

Comparisons were made in simulations, phantom experiments and neuro imaging in ten healthy volunteers, in terms of echo time ("TE") and image distortions. Results showed that EN-CODE achieved eddy current compensation with a significantly shorter TE than TRSE (78 ms vs. 96 ms) and a slightly shorter TE than MONO (78 ms vs. 80 ms). Intravoxel signal variance was lower in phantoms with EN-CODE than with MONO (13.6±11.6 vs. 37.4±25.8) and not substantially different from TRSE (15.1±11.6) indicating good robustness to eddy current induced image distortions. Mean FA values in brain edges were also significantly lower with EN-CODE than those obtained with MONO (0.16±0.01vs.0.24±0.02, p<1×10-5) and not substantially different from those obtained using TRSE (0.16±0.01vs.0.16±0.01, p=N.S.). Results herein indicate that EN-CODE eliminated eddy current induced image distortions in DTI with a TE comparable to MONO and substantially shorter than TRSE.

Methods

Simulations

EN-CODE diffusion encoding gradient waveforms were designed with a range of individual $\lambda_{null}$ (10 ms to 100 ms, $\lambda_{null}$=10 ms) using an algorithm, described with reference to FIG. 2. The range of $\lambda_{null}$ values was chosen to match the time scale of the DWI pulse sequence and corresponds with values that have been previously shown to be relevant on a clinical MRI system. The simulated pulse sequence parameters were b=1000 s/mm$^2$, bandwidth=1852 Hz/pixel (0.6 ms echo spacing), $T_e$=27.5 ms and $T_{180}$=5.2 ms, corresponding with a neuro DTI protocol with 1.7 mm in plane resolution and a 300×300 mm field of view ("FOV"). Hardware constraints were defined for a 3T MRI scanner with high performance gradients ($G_{max}$=80 mT/m and $SR_{max}$=200 T/m/s), but with $G_{max}$ limited to 76 mT/m and SRmax limited to 50 T/m/s to limit peripheral nerve stimulation during diffusion encoding. All optimizations were performed in MATLAB (Mathworks, Natick, Mass., USA) using the CPLEX linear solver (IBM, Armonk, N.Y., USA) and the YALMIP toolbox with a time-step dt=100 µs that maintained EN-CODE gradient waveform computation times to less than approximately 5 min without notably impacting the minimum possible TE.

Analogous TRSE diffusion encoding gradient waveforms were also designed using the same pulse sequence parameters and hardware constraints and with the same $\lambda_{null}$ values used for EN-CODE. Conventional MONO waveforms and non-eddy current compensated CODE waveforms were also designed. Eddy current spectra were then simulated for each diffusion encoding gradient waveform using Eqn. 5 for a range of $\lambda$ (0 ms to 100 ms, $\Delta\lambda$=1 ms) and $T_{Diff}$ matched to each sequence. TE differences between EN-CODE and alternative diffusion encoding methods were also evaluated. Minimum TEs were compared over a range of b-values (200 to 2000 s/mm$^2$) and $T_\varepsilon$ (10-60 ms) (corresponding to roughly 0.5 to 3.0 mm isotropic in-plane resolution, with full-Fourier symmetric k-space coverage) using: 1) TRSE with $\lambda_{null}$=80 ms; 2) EN-CODE with $\lambda_{null}$=80 ms; and 3) MONO. $\lambda_{null}$=80 ms was used based on the findings of the phantom imaging experiments shown below.

Phantom Imaging

Phantom experiments were performed to evaluate eddy current induced image distortions between diffusion encoding methods and to determine the optimal $\lambda_{null}$ for the present system. A phantom containing 50 mL conical tubes of water submerged in a susceptibility-matched fluid with and negligible MRI signal (Fomblin, Solvay Solexis, West Deptford, N.J.) was imaged using a 3T scanner (Prisma, Siemens, Erlangen, Germany). DWI were acquired with b=1000 s/mm$^2$ along three diffusion encoding directions (x,y,z), 1.7×1.7×5 mm spatial resolution ($T_\varepsilon$=27.5 ms), 15 interleaved slices, parallel imaging acceleration factor of two with GRAPPA, five averages to improve SNR, and TR=2300 ms (Table 1).

TABLE 1

DWI/DTI protocol detail for phantom and in vivo imaging.

| | FOV [mm] | Resolution [mm] | b [s/mm$^2$] | TR [ms] | TE [ms] | Other |
|---|---|---|---|---|---|---|
| MONO | 300 × 300 | 1.7 × 1.7 × 5.0 | 1000 | 2300 | 80 | 2× GRAPPA |
| CODE | | | | | 71 | 5 Averages |
| TRSE | | | | | 96 | 15 Slices |
| EN-CODE | | | | | 76-78 | BW = 1852 Hz/px |

All acquisition parameters were matched, except TE, for all diffusion encoding schemes: 1) MONO (TE=80 ms); 2) CODE (TE=71 ms); 3) TRSE with $\lambda_{null}$=20-100 ms (TE=96 ms); and 4) EN-CODE with $\lambda_{null}$=10-100 ms (TE=76-78 ms). A $\Delta\lambda_{null}$ of 10 ms was used for TRSE and EN-CODE. Note, $\lambda_{null}$=10 ms was not achievable for TRSE with this protocol due to timing constraints imposed by this particular $T_\varepsilon$.

Eddy current induced image distortions were evaluated for each diffusion encoding waveform by measuring the pixel-wise coefficient of variation ("CoV") across the three acquired directions. The mean global CoV ("CoV$_{Global}$") was then calculated within all water voxels (masked to exclude the very low Fomblin signal in the b=0 images) as well in edge voxels ("CoV$_{Edge}$") at water-Fomblin interfaces. The optimal $\lambda_{null}$ were determined for EN-CODE and TRSE by comparing the mean CoV$_{Edge}$ from the acquisitions with each of the ten $\lambda_{null}$ values. The $\lambda_{null}$ that led to the minimum CoV$_{Edge}$ was then used for in vivo imaging.

In Vivo Imaging

Neuro DTI were acquired in healthy volunteers (N=10) to further compare the four diffusion encoding protocols. Four DTI sets were acquired: 1) MONO; 2) CODE; 3) TRSE with $\lambda_{null}$=80 ms; and 4) EN-CODE with $\lambda_{null}$=80 ms. A $\lambda_{null}$ of 80 ms was chosen for TRSE and EN-CODE based on the phantom results (see below). The in vivo protocol was identical to the phantom study, but with 20 diffusion encoding gradient directions to facilitate tensor reconstruction (Table 1).

Images were reconstructed using manufacturer provided pipeline and no additional image registration or distortion correction was performed to correct for eddy current induced image distortion prior to off-line tensor reconstruction from each DTI set. Fractional Anisotropy ("FA") maps were then generated off-line from the diffusion tensors. The mean global FA ("FA$_{Global}$") was measured for each diffusion encoding protocol within a manually drawn whole brain mask on the b=0 images and in the outermost single-pixel layer from the global mask ("FA$_{Edge}$"). To visualize differences in eddy current induced image distortion, FA-weighted color maps of the diffusion tensor primary eigenvector (red, green and blue mapped to x, y and z) were generated for each subject. All values are reported as Mean±1SD and comparisons were made using paired t-tests wherein p-values <0.05 were deemed statistically significant.

Results

Simulations

Figure 5A:
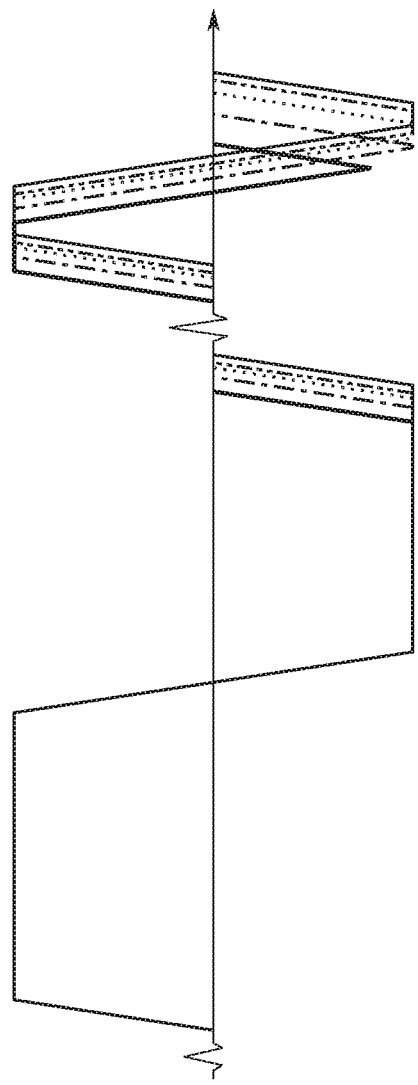
FIG. 5A is a graph showing example diffusion encoded gradient waveforms.
Figure 5B:
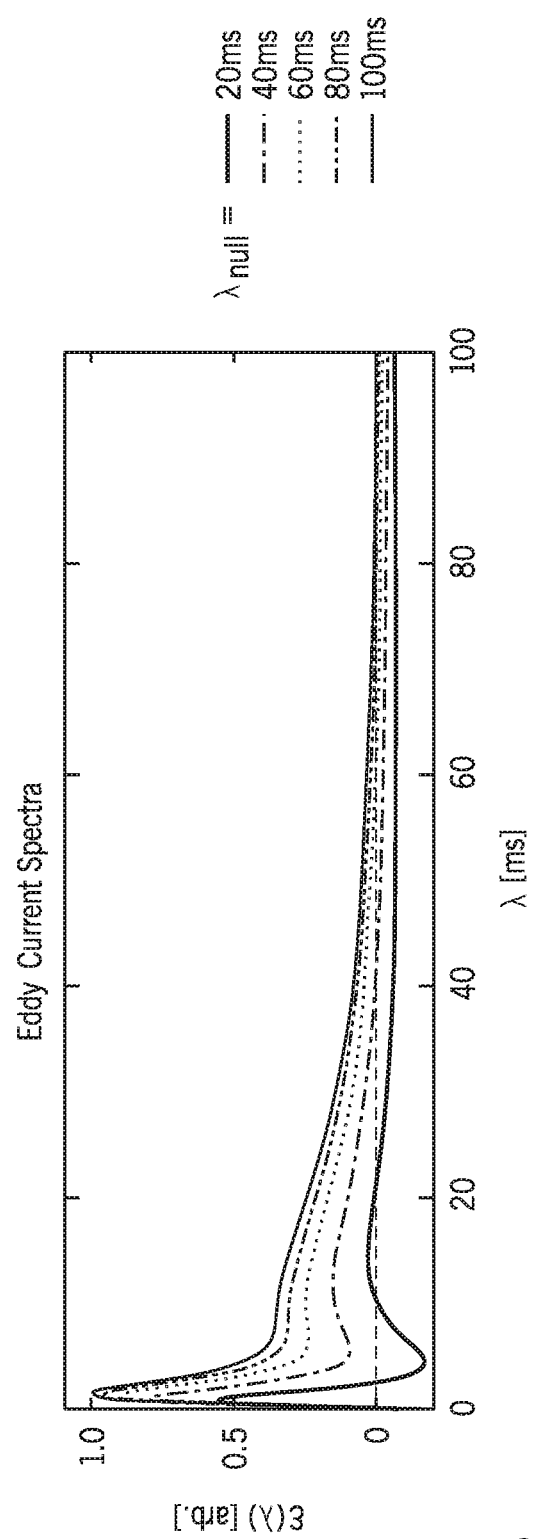
FIG. 5B is a graph showing eddy current spectra corresponding to the gradient waveforms of FIG. 5A, in accordance with aspects of the present disclosure.

FIG. 5(A) shows EN-CODE gradient waveforms generated for a range of $\lambda_{null}$ values and the corresponding eddy current spectra (B), normalized to the largest peak. Each ENCODE gradient waveform nulled eddy currents for each specified $\lambda_{null}$. Pulse sequence diagrams for MONO, CODE, TRSE with $\lambda_{null}$=80 ms and EN-CODE with $\lambda_{null}$=80 ms are shown in FIG. 6(A-D). The pulse sequence diagrams in FIG. 6 were for b=1000 s/mm$^2$ with (A) MONO, (B) CODE, (C) TRSE and (D) EN-CODE diffusion encoding. The EPI time-to-echo, T$\varepsilon$, was 27.5 ms, which accords with 1.7 mm in-plane spatial resolution (FOV=300×300 mm) for all four sequences. MONO and CODE are both susceptible to eddy current distortions, whereas TRSE and EN-CODE are eddy current compensated. EN-CODE accomplishes eddy current nulling with a slight TE decrease compared to MONO, whereas TRSE requires a significant TE increase compared with MONO.

Figure 7:
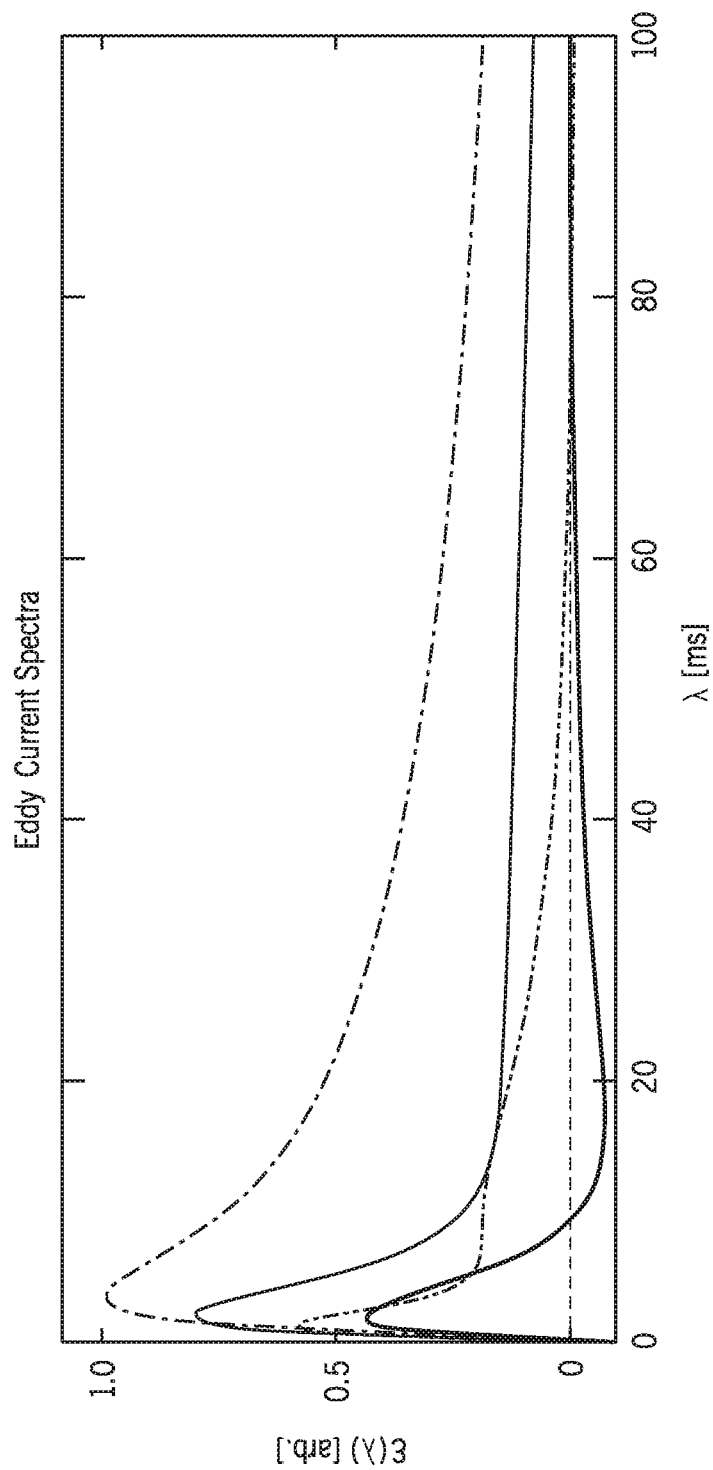
FIG. 7 is a graph showing simulated eddy current spectra at the end of diffusion encoding for a range of eddy current decay time constants for the diffusion-weighted pulse sequences of FIG. 6.
Figure 8A:
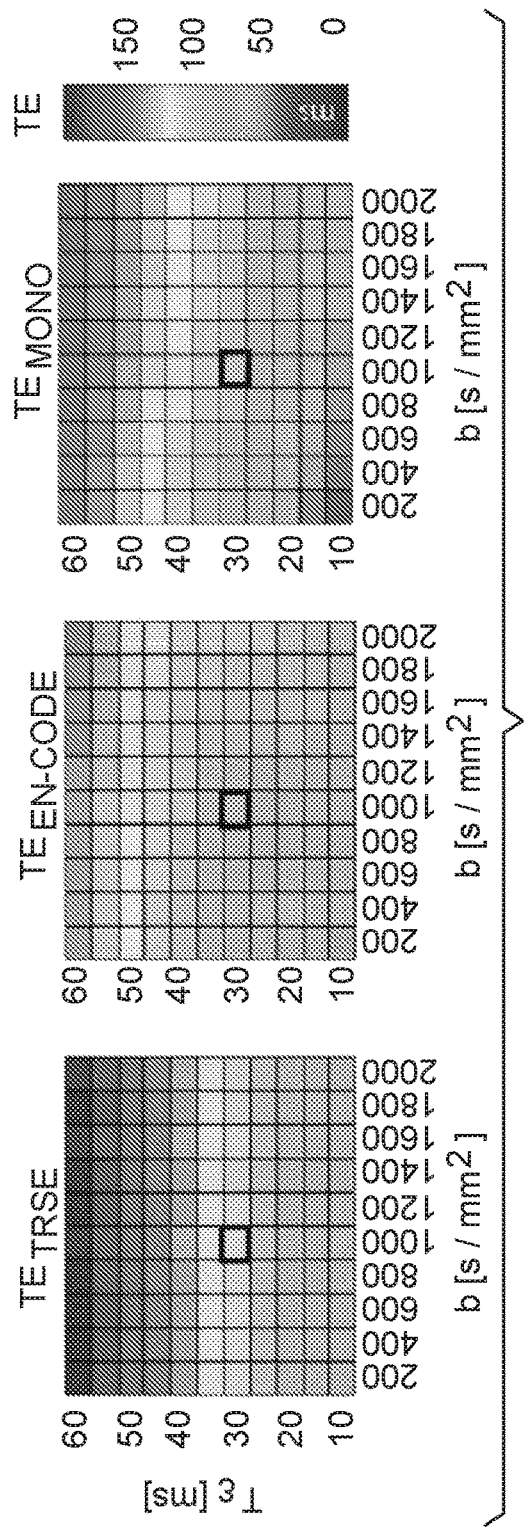
FIG. 8A shows a set of graphs indicating echo times and echo time differences function of various b-values for diffusion-weighted pulse sequences of FIG. 6.
Figure 8B:
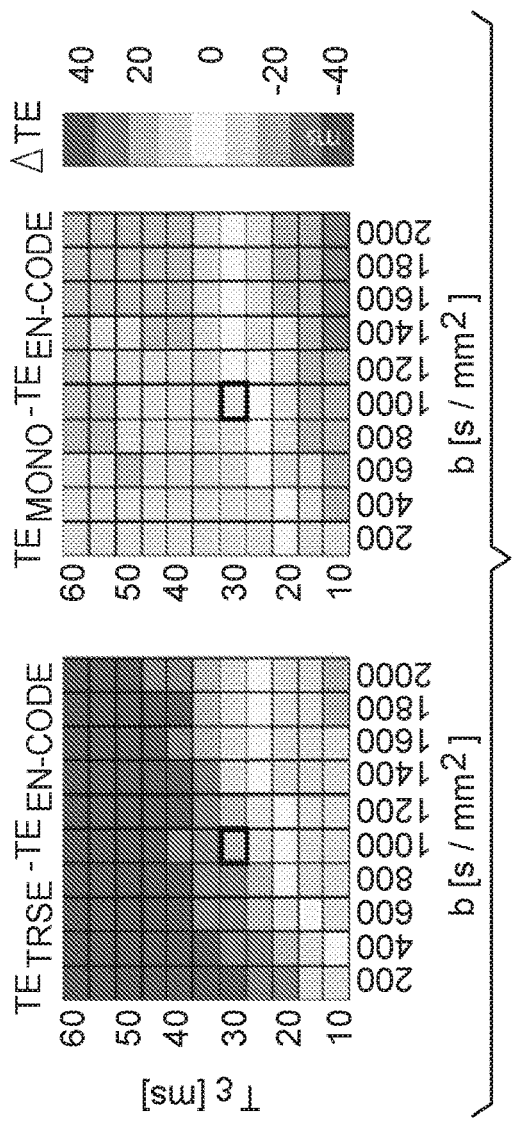
FIG. 8B shows a further set of graphs indicating echo times and echo time differences function of various b-values for diffusion-weighted pulse sequences of FIG. 6.

Each was used for both phantom and in vivo imaging. TRSE had the longest TE (96 ms) which was reduced to 80 ms with MONO, further reduced to 78 ms with EN-CODE, and minimized to 71 ms with CODE. The eddy current spectra for each sequence are shown in FIG. 7. MONO demonstrated the largest residual eddy currents across all time constants ($\lambda$) whereas CODE notably reduced eddy currents at all $\lambda$ while minimizing TE compared to the other three methods. TRSE and EN-CODE demonstrated even greater eddy current reductions, particularly for $\lambda$>20 ms. The minimum TE for TRSE ($\lambda_{null}$=80 ms), EN-CODE ($\lambda_{null}$=80 ms) and MONO over a range of b-values and T$\varepsilon$, as well as TE differences between sequences are shown in FIG. 8 shows graphs illustrating (A) The minimum TE as a function of b-value and EPI time-to-echo, T$\varepsilon$ for TRSE, EN-CODE and MONO diffusion encoding, (B) TE differences between TRSE and EN-CODE (left) as well as between MONO and EN-CODE (right). Positive values (blue) indicate EN-CODE has a shorter TE while negative values (red) indicate EN-CODE has a longer TE. EN-CODE had a shorter TE than TRSE for 78% of the examined cases (TETRSE-TEEN-CODE=20.8±18.8 ms) and a shorter TE than MONO in 65% of cases (TEMONO-TEEN-CODE=3.1±12.7 ms) while conferring eddy current insensitivity. The black square indicates the parameters used for phantom and in vivo imaging in this study and plotted in FIG. 6. The upper row (Tε=60 ms) corresponds to a DTI protocol with ~0.5 mm in-plane spatial resolution with a full-Fourier readout, the lower row (Tε=10 ms) corresponds to ~3.0 mm resolution. The choice of $\lambda_{null}$ had only a small impact on the TE for EN-CODE (the maximum TE difference between $\lambda_{null}$ values was 2 ms) and had no impact on TE for TRSE.

Figure 9:
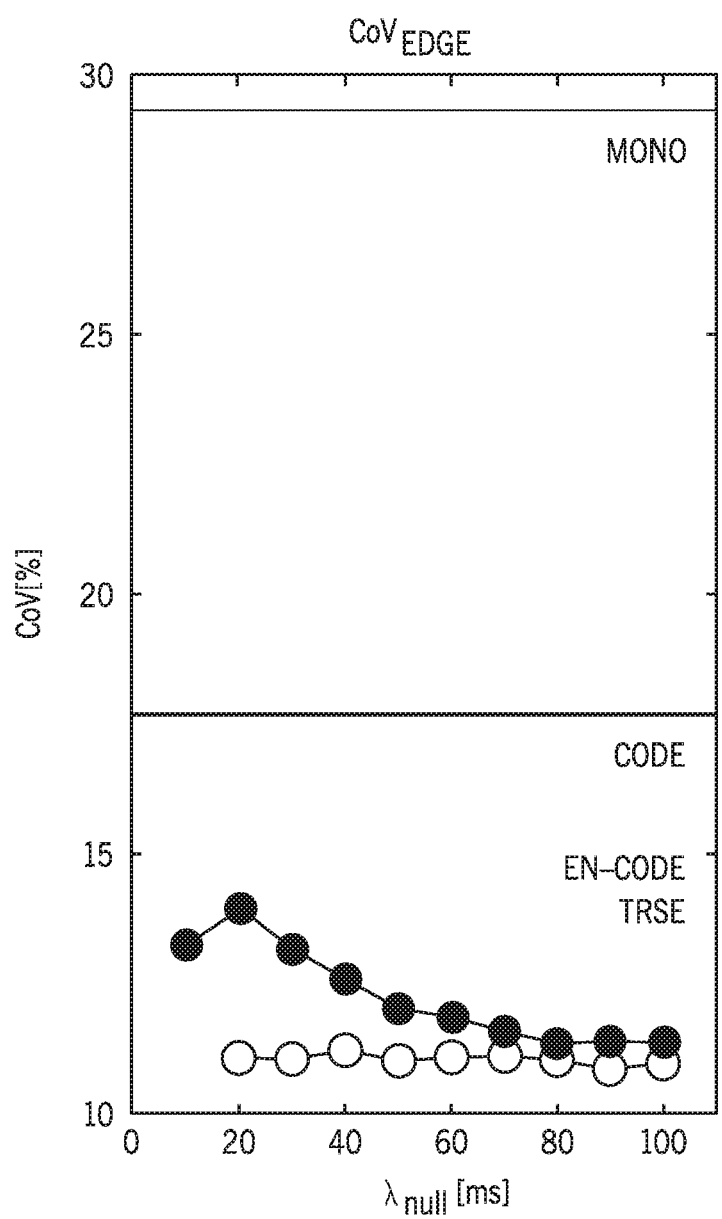
FIG. 9 is a graph comparing diffusion tensor imaging ("DTI") distortion for the diffusion-weighted pulse sequences of FIG. 6.
Figure 10A:
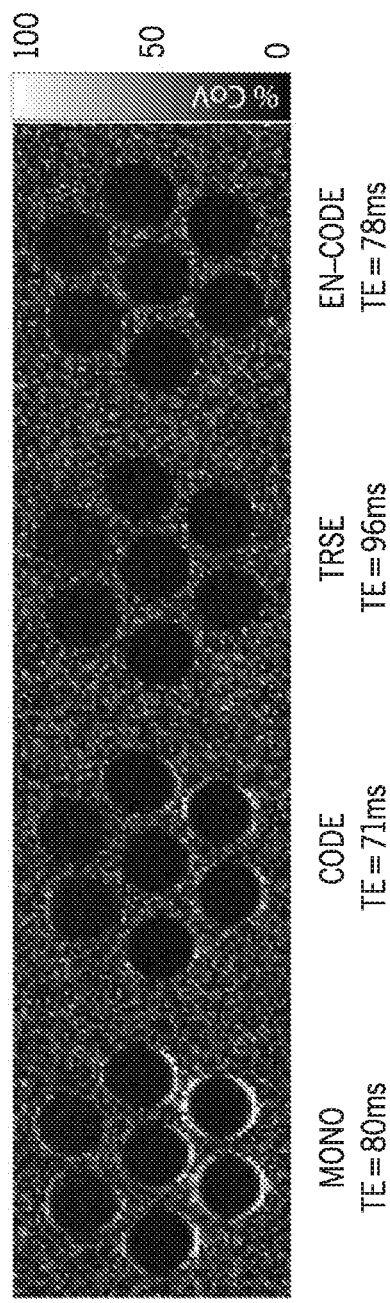
FIG. 10A is a set of images showing the coefficient of variation across direcitons.
Figure 10B:
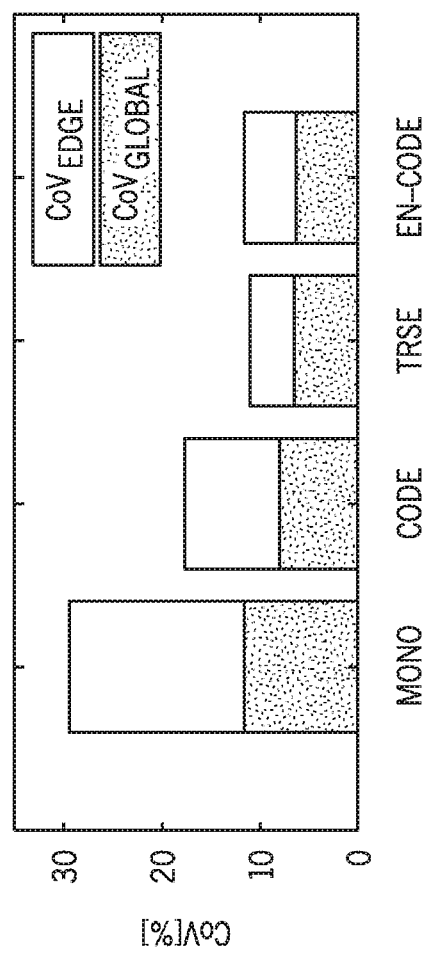
FIG. 10B are graphical illustrations comparing image distortion for the diffusion-weighted pulse sequences of FIG. 6.
Figure 10C:
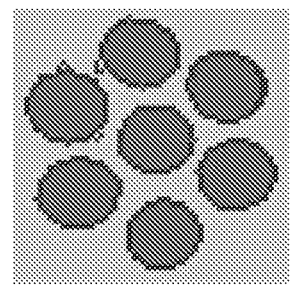
FIG. 10(C) is an image showing segmentation used for global analysis in accordance with the present disclosure.

Phantom Imaging $CoV_{Edge}$ was plotted for MONO and CODE and for TRSE and EN-CODE as a function of $\lambda_{null}$, as shown in FIG. 9. $CoV_{Edge}$ was greatest for MONO ($CoV_{Edge}$=37.4±24.5%) and reduced by 39% with CODE ($CoV_{Edge}$=22.8±18.0%). The minimum $CoV_{Edge}$ for ENCODE was achieved with $\lambda_{null}$=80 ms ($CoV_{Edge}$=13.6±11.6%), which reduced $CoV_{Edge}$ by 64% compared with MONO, and was used for subsequent in vivo imaging. TRSE demonstrated minimal variation with the choice of $\lambda_{null}$ ($CoV_{Edge}$ differences were ≤0.9% between $\lambda_{null}$ values), so $\alpha_{null}$=80 ms was also used for TRSE in vivo ($CoV_{Edge}$=15.1±11.6%). CoV maps for MONO, CODE, TRSE ($\lambda_{null}$=80 ms) and EN-CODE ($\lambda_{null}$=80 ms) in a single slice are shown in FIG. 10(A). The CoV was high for MONO near phantom edges (water-Fomblin interfaces) indicating eddy current induced misregistration between images with different diffusion encoding directions. This effect was mitigated with CODE and substantially reduced with TRSE and EN-CODE, as shown in the $COV_{Global}$ and $COV_{Edge}$ values plotted in FIG. 10(B). The segmentation used for global analysis is shown in FIG. 10(C).

In Vivo Imaging

Figure 11A:
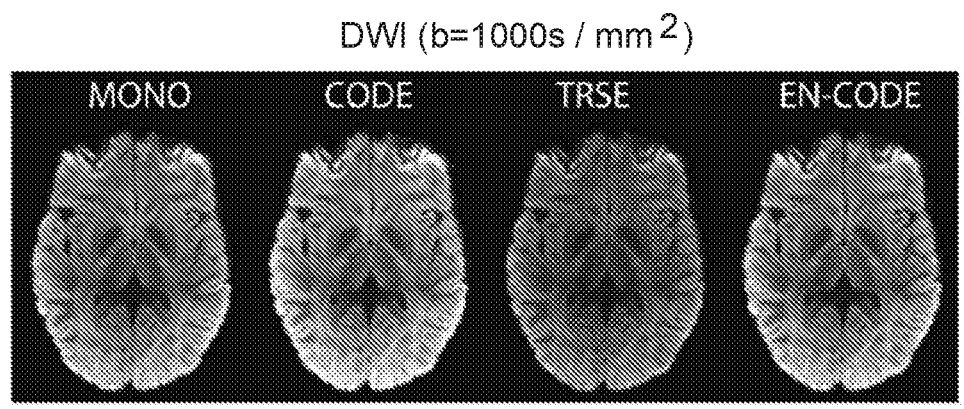
FIG. 11A is a collection of diffusion-weighted images obtained using the diffusion-weighted pulse sequences of FIG. 6.
Figure 11B:
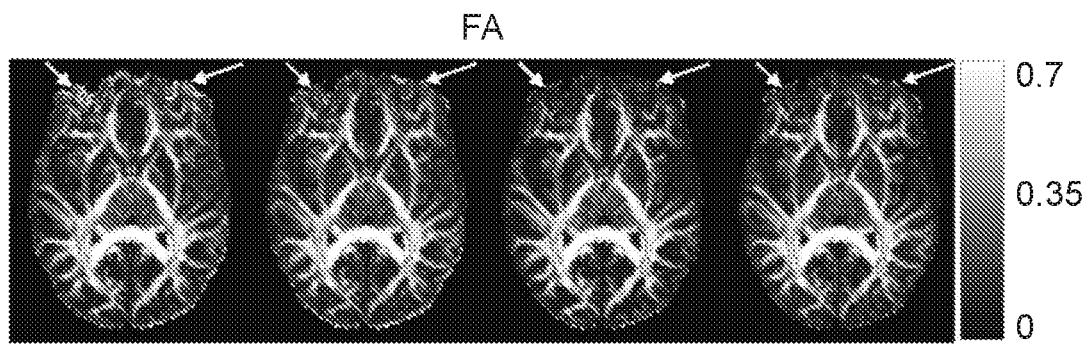
FIG. 11B is a collection of images showing fractional anisotropy created using the diffusion-weighted pulse sequence of FIG. 6.
Figure 11C:
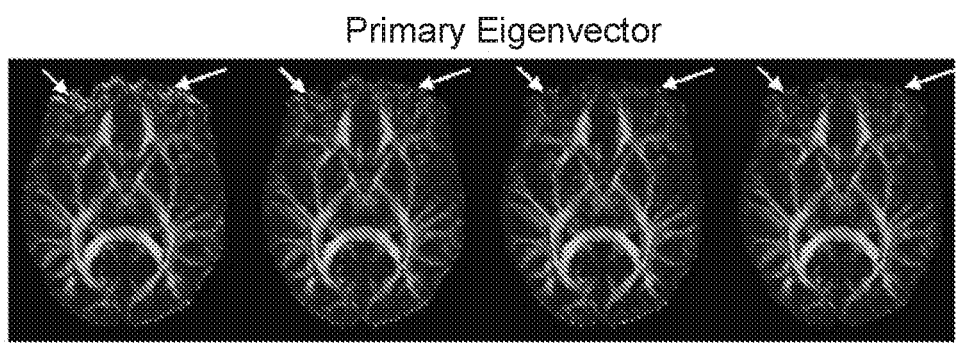
FIG. 11C is a collection of images showing primary eigenvector maps created using the diffusion-weighted pulse sequence of FIG. 6.

A representative neuro DTI example is illustrated in FIG. 11, which shows (A) diffusion weighted images from each technique, (B) reconstructed FA maps and (C) FA-weighted primary eigenvector maps where the x, y, and z vector components are mapped to red, green, and blue, respectively. MONO diffusion encoding leads to substantial eddy current image distortions that led to regions of artificially high FA (white arrows). The apparent SNR of the DWI from TRSE was lower compared to the other sequences due to the longer TE (FIG. 11 A). Eddy current distortion between diffusion encoding directions in MONO and CODE led to regions of notably elevated FA near brain edges (FIG. 11 B,C) that were largely eliminated with TRSE and EN-CODE.

Figure 12A:
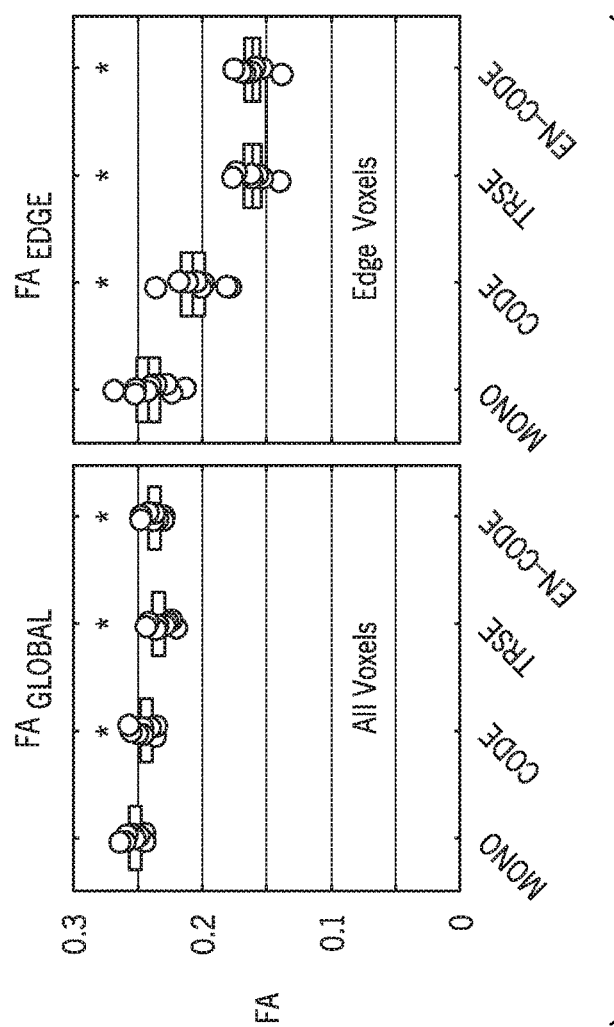
FIG. 12A is a set of graphs comparing fractional global and edge anisotropy values obtained using the diffusion-weighted pulse sequences of FIG. 6.
Figure 12B:
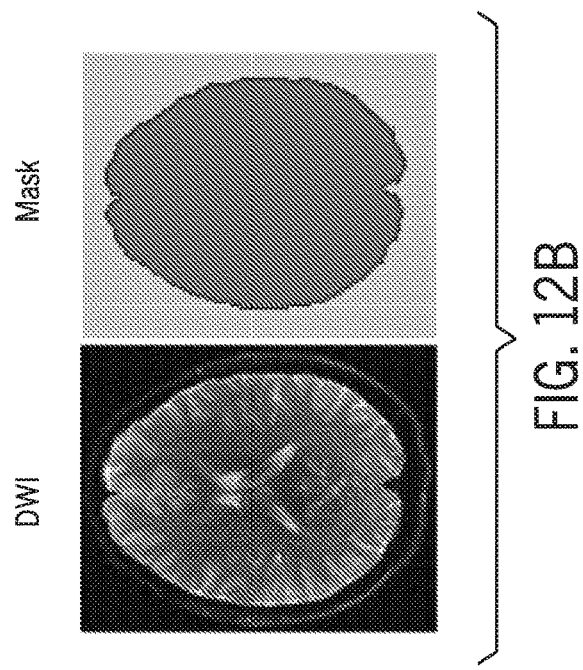
FIG. 12B is a pair of images that correlate with the graphs of FIG. 12A.

Global FA analysis is shown in FIG. 12. Specifically FIG. 12 (A) shows Mean global FA values measured in all brain voxels, $FA_{Global}$ (red) and voxels along brain edges, $FA_{Edge}$ (blue), where * indicates significant differences from MONO (p<0.05). FIG. 12 (B) also shows an example DWI and mask used for $FA_{Global}$ and $FA_{Edge}$ analysis.

As appreciated from FIG. 12, FA was reduced with CODE compared to MONO ($FA_{Global}$=0.24±0.01 vs. 0.25±0.01, p=0.02; $FA_{Edge}$=0.21±0.02 vs. 0.24±0.02, p=3×10-4). FA was further reduced with EN-CODE compared to MONO ($FA_{Global}$=0.24±0.01 vs. 0.25±0.01, p=1.5×10-4; $FA_{Edge}$=0.16±0.01 vs. 0.24±0.02, p<1×10-5). Similar FA reductions were observed with TRSE compared to MONO ($FA_{Global}$=0.23±0.01 vs.0.25±0.01, p=1×10-5; $FA_{Edge}$=0.16±0.01 vs. 0.24±0.02, p<1×10-5). There was no significant difference between TRSE and EN-CODE for either $FA_{Global}$ or $FA_{Edge}$.

Discussion

The results of the simulations, phantom imaging, and in vivo imaging all indicate that EN-CODE achieves a significant reduction of eddy current distortions compared with MONO. In the simulations, EN-CODE reduced TE compared with MONO and TRSE for a wide range of imaging and diffusion weightings parameters. Symmetric, full-Fourier k-space coverage was used in this work, but partial Fourier imaging can be used to substantially shorten Tε and thereby reduce TE, particularly for TRSE. However, the use of partial Fourier may lead to an increase in bulk-motion sensitivity, the potential for additional signal attenuation from eddy currents, a broader point-spread function, and lower SNR. EN-CODE can be used to shorten TE without the drawbacks of partial Fourier imaging. For the protocol used in this study (1.7 mm in-plane resolution, b=1000 s/mm$^2$) a partial Fourier factor of 6/8 (i.e. Tε=20.6 ms) resulted in TE=78 ms for TRSE, which is equivalent to full-Fourier EN-CODE.

While EN-CODE reduced TE compared to TRSE and MONO for a wide range of acquisition parameters, it led to longer TEs for cases with high b-values and very short (i.e. low spatial resolution, partial Fourier) EPI readouts. Although not evaluated here, the EN-CODE framework is compatible with a TRSE-like sequence which, when combined, may also confer TE reductions. Eddy current distortions in EN-CODE were more sensitive to the choice of $\lambda_{null}$ than TRSE. This may be due to the substantially lower gradient amplitudes used in TRSE than in EN-CODE ($G_{Max}$=46 mT/m for TRSE vs. 76 mT/m for EN-CODE). The use of two refocusing pulses in TRSE causes the minimum TE to be especially dictated by Tε rather than b-value (as shown by the flat TRSE TE distribution in FIG. 8), which also indicates that higher b-values could have been accomplished without increasing TE. This also led to lower slew rates for TRSE (30 T/m/s) because ramp times were fixed for all diffusion encoding gradients in the vendor-provided implementation of TRSE. Further optimization could have thus led to a slightly shorter TE for TRSE. However, even with the higher gradient amplitudes and higher slew rates, EN-CODE ($\lambda_{null}$=80 ms) achieved equivalent eddy current nulling performance to TRSE ($\lambda_{null}$=80 ms). Furthermore, the relatively flat behavior of EN-CODE for $\lambda_{null}$≥50 ms indicates that the present approach is unlikely to be sensitive to slight variations in hardware between scanners.

The in vivo neuro DTI results shown wherein demonstrate that EN-CODE improves diffusion tensor reconstruction without the need for post-processing eddy current corrections. While numerous image processing corrections exist that improve DTI reconstruction in the presence of eddy current distortions, the present eddy current nulled diffusion encoding approach avoids the added complexity and potential for errors. In addition, EN-CODE achieves this with no penalty compared to MONO over a wide range of acquisition parameters.

Although not evaluated in this work, a tripolar approach for eddy current nulling has been described previously be able to achieve reduced TE compared with TRSE. EN-CODE has similar benefits to this approach, but has the added flexibility of optimally conforming to any set of sequence parameters. Furthermore, the tripolar approach uses a gap between gradient lobes to accomplish eddy current nulling, which leads to sub-optimal diffusion encoding efficiency that extends TE. Since EN-CODE gradients are not symmetric about the refocusing pulse in this study, concomitant magnetic fields corrections may be needed to avoid significant image artifacts. A previously described linear correction was used in this work and no residual effects were observed. This approach is widely used for TRSE and was also used for CODE in this work. It is also notable that CODE, which does not explicitly account for eddy currents, improved eddy current distortions compared to MONO. CODE has previously been shown to reduce TE compared with MONO for a wide range of b-values and EPI durations indicating that the CODE gradient design is both time optimal and more robust to eddy current induced image distortion than MONO.

Features suitable for such combinations and sub-combinations would be readily apparent to persons skilled in the art upon review of the present application as a whole. The subject matter described herein and in the recited claims intends to cover and embrace all suitable changes in technology.

The invention claimed is:

1. A method for generating images using a magnetic resonance imaging ("MRI") system, the method comprising:
    a) providing a plurality of constraints comprising an eddy current constraint for imaging a target at a selected diffusion weighting;
    b) applying an optimization framework to generate an optimized diffusion encoding gradient waveform satisfying the plurality of constraints, wherein applying the optimization framework comprises performing an iterative process to minimize a timing parameter comprising a gradient duration during a diffusion encoding period;
    c) performing, using the MRI system, a pulse sequence comprising the optimized diffusion encoding gradient waveform to generate diffusion-weighted data; and
    d) generating at least one image of the target using the diffusion-weighted data.

2. The method of claim 1, wherein the eddy current constraint comprises having negligible eddy current-induced magnetic field values during readout.

3. The method of claim 1, wherein the plurality of constraints further comprises at least one of gradient constraints, gradient moment constraints, and hardware constraints.

4. The method of claim 3, wherein the gradient constraints comprise zero gradient values during a radiofrequency ("RF") activity and a readout.

5. The method of claim 3, wherein the gradient moment constraints comprise at least one of a zero moment ("M0"), a first moment ("M1"), a second moment ("M2"), a third moment ("M3") and a fourth moment ("M4") is nulled.

6. The method of claim 1, wherein applying the optimization framework at step b) further comprises performing an iterative process to minimize a timing parameter comprising an echo time ("TE").

7. The method of claim 1, wherein the target comprises at least one of a cardiac tissue, a liver tissue, and a brain tissue.

8. The method of claim 1, wherein the pulse sequence comprises a Spin-Echo Echo Planar Imaging ("SE-EPI") pulse sequence.

9. The method of claim 8, wherein a timing of a readout in the SE-EPI pulse sequence is configured based on selected field-of-view, readout bandwidth, and spatial resolution.

10. The method of claim 1, wherein the method further comprises applying the optimized diffusion encoding gradient waveform along one or more gradient field directions.

11. The method of claim 1, wherein the at least one image comprises at least one of a diffusion-weighted image ("DWI"), an apparent diffusion coefficient ("ADC") map, a diffusion tensor image ("DTI"), and a q-space image.

12. A magnetic resonance imaging ("MRI") system comprising:
    a magnet system configured to generate a polarizing magnetic field about at least a region of interest ("ROI") of a subject arranged in the MRI system;
    a plurality of gradient coils configured to apply a gradient field with respect to the polarizing magnetic field;
    a radio frequency ("RF") system configured to apply RF excitation fields to the subject and acquire MR image data therefrom; and
    a computer programmed to:
        receive an indication of a plurality of constraints comprising an eddy current constraint for imaging the ROI at a selected diffusion weighting;
        apply an optimization framework to generate an optimized diffusion encoding gradient waveform satisfying the plurality of constraints, wherein applying the optimization framework comprises performing an iterative process to minimize a timing parameter comprising a gradient duration during a diffusion encoding period;
        direct the plurality of gradient coils and RF system to perform a pulse sequence comprising the optimized diffusion encoding gradient waveform to generate diffusion-weighted data; and
        generate at least one image of the target using the diffusion-weighted data.

13. The system of claim 12, wherein the eddy current constraint comprises having negligible gradient-induced magnetic field values during readout.

14. The system of claim 12, wherein the plurality of constraints further comprises at least one of gradient constraints, gradient moment constraints, and hardware constraints.

15. The system of claim 12, wherein the gradient constraints comprise zero gradient values during a radiofrequency ("RF") activity and a readout.

16. The system of claim 12, wherein the gradient moment constraints comprise at least one of a zero moment ("M0"), a first moment ("M1"), a second moment ("M2"), a third moment ("M3") and a fourth moment ("M4") is nulled.

17. The system of claim 12, wherein computer is further programmed to perform an iterative process to minimize a timing parameter comprising an echo time ("TE").

18. The system of claim 12, wherein the ROI comprises at least one of a cardiac tissue, a liver tissue, and a brain tissue.

19. The system of claim 12, wherein computer is further programmed to perform a Spin-Echo Echo Planar Imaging ("SE-EPI") pulse sequence.

20. The system of claim 19, wherein a timing of a readout in the SE-EPI pulse sequence is configured based on selected field-of-view, readout bandwidth, and spatial resolution.

21. The system of claim 12, wherein the computer is further programmed to apply the optimized diffusion encoding gradient waveform along one or more gradient field directions.

22. The system of claim 12, wherein the at least one image comprises at least one of a diffusion-weighted image ("DWI"), an apparent diffusion coefficient ("ADC") map, a diffusion tensor image ("DTI"), and a q-space image.

23. The system of claim 12, wherein the optimization framework comprises a convex optimization framework or a non-convex optimization framework.

* * * * *

UNITED STATES PATENT AND TRADEMARK OFFICE
CERTIFICATE OF CORRECTION

PATENT NO.         : 11,137,467 B2
APPLICATION NO.    : 16/488972
DATED              : October 5, 2021
INVENTOR(S)        : Daniel Ennis et al.

Page 1 of 1

It is certified that error appears in the above-identified patent and that said Letters Patent is hereby corrected as shown below:

In the Specification

Column 17, Line 22, "COV $_{Edge}$" should be --CoV$_{Edge}$--.

Column 17, Line 24, "COV $_{Edge}$" should be --CoV$_{Edge}$--.

Column 17, Line 32, "COV $_{Global}$ and COV $_{Edge}$" should be --CoV$_{Global}$ and CoV$_{Edge}$--.

Signed and Sealed this
Fourth Day of January, 2022

Drew Hirshfeld
*Performing the Functions and Duties of the*
*Under Secretary of Commerce for Intellectual Property and*
*Director of the United States Patent and Trademark Office*